United States Patent
Benn

(10) Patent No.: US 9,989,507 B2
(45) Date of Patent: Jun. 5, 2018

(54) DETECTION AND PREVENTION OF TOXIC GAS

(71) Applicant: EchoStar UK Holdings Limited, Steeton (GB)

(72) Inventor: Mala Benn, North Yorkshire (GB)

(73) Assignee: EchoStar Technologies International Corporation, Englewood, CO (US)

(*) Notice: Subject to any disclaimer, the term of this patent is extended or adjusted under 35 U.S.C. 154(b) by 433 days.

(21) Appl. No.: 14/497,130

(22) Filed: Sep. 25, 2014

(65) Prior Publication Data

US 2016/0091471 A1    Mar. 31, 2016

(51) Int. Cl.
| | |
|---|---|
| G01K 13/00 | (2006.01) |
| G01N 33/00 | (2006.01) |
| G01W 1/00 | (2006.01) |
| G05B 19/048 | (2006.01) |
| G05B 15/02 | (2006.01) |

(Continued)

(52) U.S. Cl.
CPC ........ *G01N 33/004* (2013.01); *F24F 11/0086* (2013.01); *G01K 13/00* (2013.01); *G01N 33/0004* (2013.01); *G01W 1/00* (2013.01); *G05B 15/02* (2013.01); *G05B 19/048* (2013.01); *F24F 2011/0027* (2013.01); *G05B 2219/23238* (2013.01); *G05B 2219/2642* (2013.01);

(Continued)

(58) Field of Classification Search
CPC ............... H04L 12/2803; H04L 12/282; H04L 12/2827; G08B 21/14; G08B 25/008; G08B 17/10; G01N 33/004

USPC .......... 340/501, 506, 628; 379/37; 702/188; 700/275, 278

See application file for complete search history.

(56) References Cited

U.S. PATENT DOCUMENTS

| | | |
|---|---|---|
| 4,127,966 A | 12/1978 | Schmidt |
| 4,386,436 A | 5/1983 | Kocher et al. |

(Continued)

FOREIGN PATENT DOCUMENTS

| | | |
|---|---|---|
| CA | 2 267 988 A1 | 4/1998 |
| CN | 105814555 A | 7/2016 |

(Continued)

OTHER PUBLICATIONS

Fong A.C.M. et al, "Indoor air quality control for asthma patients using smart home technology," Consumer Electronics (ISCE), 2011 IEEE 15th International Symposium on, IEEE, Jun. 14, 2011, pp. 18-19, XP032007803, DOI: 10.1109/ISCE.2011.5973774, ISBN: 978-1-61284-843-3, Abstract and sections 3 and 4.

(Continued)

*Primary Examiner* — Roy Y Yi
*Assistant Examiner* — Jeffrey Aiello
(74) *Attorney, Agent, or Firm* — Kilpatrick Townsend & Stockton LLP

(57) ABSTRACT

Various arrangements for detecting and mitigating toxic gases are presented. Components of a home automation system may be used to monitor gas concentrations in home. Changes or elevated levels of gas concentrations may trigger mitigation or diagnosis procedures. Diagnosis procedures may include correlating the gas sensor readings with the activity of components of a home to identify possible causality. The activity of components may be changed and altered to test correlations or determine causality between components.

20 Claims, 8 Drawing Sheets

(51) Int. Cl.
  *H04N 21/41* (2011.01)
  *F24F 11/00* (2018.01)
  *H04N 21/442* (2011.01)

(52) U.S. Cl.
  CPC ... *H04N 21/4131* (2013.01); *H04N 21/44231* (2013.01); *Y02B 30/78* (2013.01)

(56) References Cited

U.S. PATENT DOCUMENTS

| | | |
|---|---|---|
| 4,581,606 A | 4/1986 | Mallory |
| 4,694,607 A | 9/1987 | Ishida et al. |
| 4,728,949 A | 3/1988 | Platte et al. |
| 4,959,713 A | 9/1990 | Morotomi et al. |
| 5,400,246 A | 3/1995 | Wilson et al. |
| 5,770,896 A | 6/1998 | Nakajima |
| 5,805,442 A | 9/1998 | Crater et al. |
| 5,822,012 A | 10/1998 | Jeon et al. |
| 5,886,638 A * | 3/1999 | Tanguay .......... G08B 17/10 340/628 |
| 5,894,331 A | 4/1999 | Yang |
| 5,926,090 A | 7/1999 | Taylor et al. |
| 5,970,030 A | 10/1999 | Dimitri et al. |
| 6,081,758 A | 6/2000 | Parvulescu |
| 6,104,334 A | 8/2000 | Allport |
| 6,107,918 A | 8/2000 | Klein et al. |
| 6,107,935 A | 8/2000 | Comerford et al. |
| 6,111,517 A | 8/2000 | Atick et al. |
| 6,119,088 A | 9/2000 | Ciluffo |
| 6,142,913 A | 11/2000 | Ewert |
| 6,182,094 B1 | 1/2001 | Humpleman et al. |
| 6,225,938 B1 | 5/2001 | Hayes et al. |
| 6,286,764 B1 | 9/2001 | Garvey et al. |
| 6,330,621 B1 | 12/2001 | Bakke et al. |
| 6,337,899 B1 | 1/2002 | Alcendor et al. |
| 6,377,858 B1 | 4/2002 | Koeppe |
| 6,405,284 B1 | 6/2002 | Bridge |
| 6,415,257 B1 | 7/2002 | Jungua et al. |
| 6,502,166 B1 | 12/2002 | Cassidy |
| 6,529,230 B1 | 3/2003 | Chong |
| 6,543,051 B1 | 4/2003 | Manson et al. |
| 6,553,375 B1 | 4/2003 | Huang et al. |
| 6,663,375 B1 | 8/2003 | Huang et al. |
| 6,646,676 B1 | 11/2003 | DaGraca et al. |
| 6,662,282 B2 | 12/2003 | Cochran |
| 6,744,771 B1 | 6/2004 | Barber et al. |
| 6,748,343 B2 | 6/2004 | Alexander et al. |
| 6,751,657 B1 | 6/2004 | Zothner |
| 6,756,998 B1 | 6/2004 | Bilger |
| 6,792,319 B1 | 9/2004 | Bilger |
| 6,876,889 B1 | 4/2005 | Lortz et al. |
| 6,891,838 B1 | 5/2005 | Petite et al. |
| 6,931,104 B1 | 8/2005 | Foster et al. |
| 6,976,187 B2 | 12/2005 | Arnott et al. |
| 6,989,731 B1 | 1/2006 | Kawai et al. |
| 7,009,528 B2 | 3/2006 | Griep |
| 7,010,332 B1 | 3/2006 | Irvin et al. |
| 7,088,238 B2 | 8/2006 | Karaoguz et al. |
| 7,103,545 B2 | 9/2006 | Furuta |
| 7,143,298 B2 | 11/2006 | Wells et al. |
| 7,216,002 B1 | 5/2007 | Anderson |
| 7,234,074 B2 | 6/2007 | Cohn et al. |
| 7,260,538 B2 | 8/2007 | Calderone et al. |
| 7,346,917 B2 | 3/2008 | Gatto et al. |
| 7,372,370 B2 | 5/2008 | Stults et al. |
| 7,386,666 B1 | 6/2008 | Beauchamp et al. |
| 7,391,319 B1 | 6/2008 | Walker |
| 7,395,369 B2 | 7/2008 | Sepez et al. |
| 7,395,546 B1 | 7/2008 | Asmussen |
| 7,529,677 B1 | 5/2009 | Wittenberg |
| 7,574,494 B1 | 8/2009 | Mayernick et al. |
| 7,579,945 B1 | 8/2009 | Richter et al. |
| 7,590,703 B2 | 9/2009 | Cashman et al. |
| 7,640,351 B2 | 12/2009 | Reckamp et al. |
| 7,659,814 B2 | 2/2010 | Chen et al. |
| 7,694,005 B2 | 4/2010 | Reckamp et al. |
| 7,739,718 B1 | 6/2010 | Young et al. |
| 7,861,034 B2 | 12/2010 | Yamamoto et al. |
| 7,870,232 B2 | 1/2011 | Reckamp et al. |
| 7,945,297 B2 | 5/2011 | Philipp |
| 7,969,318 B2 | 6/2011 | White et al. |
| 8,013,730 B2 | 9/2011 | Oh et al. |
| 8,042,048 B2 | 10/2011 | Wilson et al. |
| 8,086,757 B2 | 12/2011 | Chang |
| 8,106,768 B2 | 1/2012 | Neumann |
| 8,156,368 B2 | 4/2012 | Chambliss et al. |
| 8,171,148 B2 | 4/2012 | Lucas et al. |
| 8,180,735 B2 | 5/2012 | Ansari et al. |
| 8,201,261 B2 | 6/2012 | Barfield et al. |
| 8,221,290 B2 | 7/2012 | Vincent et al. |
| 8,275,143 B2 | 9/2012 | Johnson |
| 8,289,157 B2 | 10/2012 | Patenaude et al. |
| 8,290,545 B2 | 10/2012 | Terlizzi |
| 8,310,335 B2 | 11/2012 | Sivakkolundhu |
| 8,316,413 B2 | 11/2012 | Crabtree |
| 8,320,578 B2 | 11/2012 | Kahn et al. |
| 8,335,312 B2 | 12/2012 | Gerhardt et al. |
| 8,350,694 B1 | 1/2013 | Trundle et al. |
| 8,413,204 B2 | 4/2013 | White et al. |
| 8,436,902 B2 | 5/2013 | Kuehnle |
| 8,498,572 B1 | 7/2013 | Schooley et al. |
| 8,516,087 B2 | 8/2013 | Wilson et al. |
| 8,539,567 B1 | 9/2013 | Logue et al. |
| 8,550,368 B2 | 10/2013 | Butler et al. |
| 8,619,136 B2 | 12/2013 | Howarter et al. |
| 8,620,841 B1 * | 12/2013 | Filson .............. H04L 12/1895 706/12 |
| 8,644,525 B2 | 2/2014 | Bathurst et al. |
| 8,645,327 B2 | 2/2014 | Falkenburg et al. |
| 8,667,529 B2 | 3/2014 | Taxier |
| 8,750,576 B2 | 6/2014 | Huang et al. |
| 8,780,201 B1 | 7/2014 | Scalisi et al. |
| 8,781,508 B1 | 7/2014 | Blakely |
| 8,786,698 B2 | 7/2014 | Chen et al. |
| 8,799,413 B2 | 8/2014 | Taylor et al. |
| 8,818,898 B2 | 8/2014 | Schlossberg et al. |
| 8,898,709 B2 | 11/2014 | Crabtree |
| 8,923,823 B1 | 12/2014 | Wilde |
| 8,930,700 B2 | 1/2015 | Wielopolski |
| 8,948,793 B1 | 2/2015 | Birkhold et al. |
| 8,965,170 B1 | 2/2015 | Benea et al. |
| 9,019,111 B1 | 4/2015 | Sloo et al. |
| 9,049,567 B2 | 6/2015 | Le Guen et al. |
| 9,191,804 B1 | 11/2015 | Paczkowski et al. |
| 9,237,141 B2 | 1/2016 | Logue et al. |
| 9,246,921 B1 | 1/2016 | Vlaminck et al. |
| 9,258,593 B1 | 2/2016 | Chen et al. |
| 9,286,482 B1 | 3/2016 | Dumont et al. |
| 9,353,500 B1 | 5/2016 | Andreski |
| 9,443,142 B2 | 9/2016 | Reynolds, Jr. |
| 9,462,041 B1 | 10/2016 | Hagins et al. |
| 9,495,860 B2 | 11/2016 | Lett |
| 9,511,259 B2 | 12/2016 | Mountain |
| 9,589,448 B1 | 3/2017 | Schneider et al. |
| 9,599,981 B2 | 3/2017 | Crabtree |
| 9,621,959 B2 | 4/2017 | Mountain |
| 9,628,286 B1 | 4/2017 | Nguyen et al. |
| 9,632,746 B2 | 4/2017 | Keipert et al. |
| 9,633,186 B2 | 4/2017 | Ingrassia, Jr. et al. |
| 9,729,989 B2 | 8/2017 | Marten |
| 9,772,612 B2 | 9/2017 | McCarthy et al. |
| 9,798,309 B2 | 10/2017 | Tirpak |
| 9,824,578 B2 | 11/2017 | Burton et al. |
| 9,838,736 B2 | 12/2017 | Smith et al. |
| 9,882,736 B2 | 1/2018 | Lett |
| 2001/0012998 A1 | 8/2001 | Jouet et al. |
| 2002/0003493 A1 | 1/2002 | Durst et al. |
| 2002/0019725 A1 | 2/2002 | Petite |
| 2002/0063633 A1 | 5/2002 | Park |
| 2002/0080238 A1 | 6/2002 | Ohmura |
| 2002/0193989 A1 | 12/2002 | Geilhufe et al. |
| 2003/0005431 A1 | 1/2003 | Shinohara |
| 2003/0052789 A1 | 3/2003 | Colmenarez et al. |
| 2003/0097452 A1 | 5/2003 | Kim et al. |
| 2003/0126593 A1 | 7/2003 | Mault |

(56) References Cited

U.S. PATENT DOCUMENTS

| | | |
|---|---|---|
| 2003/0133551 A1 | 7/2003 | Kahn |
| 2003/0140352 A1 | 7/2003 | Kim |
| 2003/0154242 A1 | 8/2003 | Hayes et al. |
| 2003/0192600 A1 | 10/2003 | Ford |
| 2003/0201900 A1 | 10/2003 | Bachinski et al. |
| 2004/0019489 A1 | 1/2004 | Funk et al. |
| 2004/0036579 A1 | 2/2004 | Megerle |
| 2004/0117038 A1 | 6/2004 | Karaoguz et al. |
| 2004/0117843 A1 | 6/2004 | Karaoguz et al. |
| 2004/0121725 A1 | 6/2004 | Matsui |
| 2004/0128034 A1 | 7/2004 | Lenker et al. |
| 2004/0143838 A1 | 7/2004 | Rose |
| 2004/0148419 A1 | 7/2004 | Chen et al. |
| 2004/0148632 A1 | 7/2004 | Park et al. |
| 2004/0260407 A1 | 12/2004 | Wimsatt |
| 2004/0266419 A1 | 12/2004 | Arling et al. |
| 2005/0038875 A1 | 2/2005 | Park |
| 2005/0049862 A1 | 3/2005 | Choi et al. |
| 2005/0106267 A1* | 5/2005 | Frykman ............. A61K 45/06 424/684 |
| 2005/0159823 A1 | 7/2005 | Hayes et al. |
| 2005/0188315 A1 | 8/2005 | Campbell et al. |
| 2005/0200478 A1 | 9/2005 | Koch et al. |
| 2005/0245292 A1 | 11/2005 | Bennett et al. |
| 2005/0252622 A1 | 11/2005 | Reid |
| 2005/0264698 A1 | 12/2005 | Eshleman |
| 2005/0289614 A1 | 12/2005 | Baek et al. |
| 2006/0011145 A1 | 1/2006 | Kates |
| 2006/0059977 A1* | 3/2006 | Kates ................. G01M 3/2815 73/40 |
| 2006/0087428 A1 | 4/2006 | Wolfe et al. |
| 2006/0115156 A1 | 6/2006 | Nakajima et al. |
| 2006/0136968 A1 | 6/2006 | Han et al. |
| 2006/0143679 A1 | 6/2006 | Yamada et al. |
| 2006/0155389 A1 | 7/2006 | Pessolano et al. |
| 2006/0186740 A1 | 8/2006 | Von Gunten |
| 2006/0192680 A1* | 8/2006 | Scuka ................ G08B 26/002 340/632 |
| 2006/0244624 A1 | 11/2006 | Wang et al. |
| 2006/0253894 A1 | 11/2006 | Bookman et al. |
| 2007/0044119 A1 | 2/2007 | Sullivan et al. |
| 2007/0078910 A1 | 4/2007 | Bopardikar |
| 2007/0129220 A1 | 6/2007 | Bardha |
| 2007/0135225 A1 | 6/2007 | Nieminen et al. |
| 2007/0142022 A1 | 6/2007 | Madonna et al. |
| 2007/0146545 A1 | 6/2007 | Iwahashi |
| 2007/0150460 A1* | 6/2007 | Evans ................ A63B 29/021 |
| 2007/0157258 A1 | 7/2007 | Jung et al. |
| 2007/0192486 A1 | 8/2007 | Wilson et al. |
| 2007/0194922 A1 | 8/2007 | Nathan et al. |
| 2007/0256085 A1 | 11/2007 | Reckamp et al. |
| 2007/0271518 A1 | 11/2007 | Tischer et al. |
| 2007/0275670 A1 | 11/2007 | Chen et al. |
| 2007/0279244 A1 | 12/2007 | Haughawout et al. |
| 2007/0280504 A1 | 12/2007 | Badawy et al. |
| 2008/0019392 A1 | 1/2008 | Lee |
| 2008/0021971 A1 | 1/2008 | Halgas |
| 2008/0022322 A1 | 1/2008 | Grannan et al. |
| 2008/0046930 A1 | 2/2008 | Smith et al. |
| 2008/0062258 A1 | 3/2008 | Bentkovski et al. |
| 2008/0062965 A1 | 3/2008 | Silva et al. |
| 2008/0092199 A1 | 4/2008 | McCarthy et al. |
| 2008/0109095 A1 | 5/2008 | Braithwaite et al. |
| 2008/0114963 A1 | 5/2008 | Cannon et al. |
| 2008/0120639 A1 | 5/2008 | Walter et al. |
| 2008/0123825 A1 | 5/2008 | Abramson et al. |
| 2008/0140736 A1 | 6/2008 | Jarno |
| 2008/0144884 A1 | 6/2008 | Habibi |
| 2008/0163330 A1 | 7/2008 | Sparrell |
| 2008/0179053 A1 | 7/2008 | Kates |
| 2008/0236214 A1 | 10/2008 | Han |
| 2008/0278635 A1 | 11/2008 | Hardacker et al. |
| 2008/0284905 A1 | 11/2008 | Chuang |
| 2008/0288876 A1 | 11/2008 | Fleming |
| 2008/0297660 A1 | 12/2008 | Shioya |
| 2009/0023554 A1 | 1/2009 | Shim |
| 2009/0027225 A1 | 1/2009 | Farley |
| 2009/0033505 A1 | 2/2009 | Jones et al. |
| 2009/0040013 A1 | 2/2009 | Ebrom et al. |
| 2009/0066320 A1 | 3/2009 | Posey |
| 2009/0069038 A1 | 3/2009 | Olague et al. |
| 2009/0083374 A1 | 3/2009 | Saint Clair |
| 2009/0112541 A1 | 4/2009 | Anderson et al. |
| 2009/0138507 A1 | 5/2009 | Burckart et al. |
| 2009/0146834 A1 | 6/2009 | Huang |
| 2009/0165069 A1 | 6/2009 | Kirchner |
| 2009/0167555 A1 | 7/2009 | Kohanek |
| 2009/0190040 A1 | 7/2009 | Watanabe et al. |
| 2009/0235992 A1 | 9/2009 | Armstrong |
| 2009/0249428 A1 | 10/2009 | White et al. |
| 2009/0270065 A1 | 10/2009 | Hamada et al. |
| 2009/0271203 A1 | 10/2009 | Resch et al. |
| 2009/0286654 A1 | 11/2009 | Rice |
| 2009/0307715 A1 | 12/2009 | Santamaria et al. |
| 2010/0031286 A1 | 2/2010 | Gupta et al. |
| 2010/0045471 A1 | 2/2010 | Meyers |
| 2010/0046918 A1 | 2/2010 | Takao et al. |
| 2010/0066507 A1 | 3/2010 | Myllymaki |
| 2010/0083371 A1 | 4/2010 | Bennetts et al. |
| 2010/0097225 A1 | 4/2010 | Petricoin, Jr. |
| 2010/0102082 A1 | 4/2010 | Ebrom et al. |
| 2010/0122284 A1 | 5/2010 | Yoon et al. |
| 2010/0131280 A1 | 5/2010 | Bogineni |
| 2010/0138007 A1 | 6/2010 | Clark et al. |
| 2010/0138858 A1 | 6/2010 | Velazquez et al. |
| 2010/0146445 A1 | 6/2010 | Kraut |
| 2010/0161082 A1 | 6/2010 | Ebrom et al. |
| 2010/0164732 A1 | 7/2010 | Wedig et al. |
| 2010/0211546 A1 | 8/2010 | Grohman et al. |
| 2010/0277300 A1 | 11/2010 | Cohn et al. |
| 2010/0283579 A1 | 11/2010 | Kraus et al. |
| 2010/0309004 A1 | 12/2010 | Grundler et al. |
| 2010/0321151 A1 | 12/2010 | Matsuura et al. |
| 2011/0003665 A1 | 1/2011 | Burton et al. |
| 2011/0018693 A1 | 1/2011 | Lim et al. |
| 2011/0030016 A1 | 2/2011 | Pino et al. |
| 2011/0032423 A1 | 2/2011 | Jing et al. |
| 2011/0093126 A1 | 4/2011 | Toba et al. |
| 2011/0119325 A1 | 5/2011 | Paul et al. |
| 2011/0139076 A1 | 6/2011 | Pu et al. |
| 2011/0140832 A1 | 6/2011 | Vinkenvleugel et al. |
| 2011/0150432 A1 | 6/2011 | Paul et al. |
| 2011/0156862 A1 | 6/2011 | Langer |
| 2011/0157468 A1 | 6/2011 | Dai |
| 2011/0167250 A1 | 7/2011 | Dicks et al. |
| 2011/0187928 A1 | 8/2011 | Crabtree |
| 2011/0187930 A1 | 8/2011 | Crabtree |
| 2011/0187931 A1 | 8/2011 | Kim |
| 2011/0202956 A1 | 8/2011 | Connelly et al. |
| 2011/0267180 A1 | 11/2011 | Ferringo et al. |
| 2011/0270549 A1 | 11/2011 | Jeansonne et al. |
| 2011/0282837 A1 | 11/2011 | Gounares et al. |
| 2011/0283311 A1 | 11/2011 | Luong |
| 2011/0285528 A1 | 11/2011 | Weinstein et al. |
| 2011/0295396 A1 | 12/2011 | Chinen et al. |
| 2011/0296463 A1 | 12/2011 | Suslov |
| 2012/0019388 A1 | 1/2012 | Kates |
| 2012/0047083 A1 | 2/2012 | Qiao et al. |
| 2012/0047532 A1 | 2/2012 | McCarthy |
| 2012/0059495 A1 | 3/2012 | Weiss et al. |
| 2012/0069246 A1 | 3/2012 | Thornberry et al. |
| 2012/0092183 A1 | 4/2012 | Corbett et al. |
| 2012/0094696 A1 | 4/2012 | Ahn et al. |
| 2012/0105724 A1 | 5/2012 | Candelore |
| 2012/0124245 A1 | 5/2012 | Reeves et al. |
| 2012/0124456 A1 | 5/2012 | Perez et al. |
| 2012/0154108 A1 | 6/2012 | Sugaya |
| 2012/0154138 A1 | 6/2012 | Cohn et al. |
| 2012/0164975 A1 | 6/2012 | Dodeja et al. |
| 2012/0167646 A1 | 7/2012 | Sharma et al. |
| 2012/0226366 A1 | 9/2012 | Lee et al. |
| 2012/0226768 A1 | 9/2012 | Gaines et al. |
| 2012/0271472 A1 | 10/2012 | Brunner et al. |
| 2012/0271670 A1 | 10/2012 | Zaloom |

(56) References Cited

U.S. PATENT DOCUMENTS

| | | |
|---|---|---|
| 2012/0280802 A1 | 11/2012 | Yoshida et al. |
| 2012/0291068 A1 | 11/2012 | Khushoo et al. |
| 2012/0314713 A1 | 12/2012 | Singh et al. |
| 2012/0316876 A1 | 12/2012 | Jang et al. |
| 2012/0326835 A1 | 12/2012 | Cockrell et al. |
| 2013/0006400 A1 | 1/2013 | Caceres et al. |
| 2013/0013106 A1 | 1/2013 | Carelli et al. |
| 2013/0031037 A1 | 1/2013 | Brandt et al. |
| 2013/0046800 A1 | 2/2013 | Assi et al. |
| 2013/0049950 A1 | 2/2013 | Wohlert |
| 2013/0053063 A1 | 2/2013 | McSheffrey |
| 2013/0060358 A1 | 3/2013 | Li et al. |
| 2013/0070044 A1 | 3/2013 | Naidoo et al. |
| 2013/0074061 A1 | 3/2013 | Averbuch et al. |
| 2013/0090213 A1 | 4/2013 | Amini et al. |
| 2013/0120137 A1 | 5/2013 | Lehmann |
| 2013/0124192 A1 | 5/2013 | Lindmark et al. |
| 2013/0138757 A1 | 5/2013 | Ferron |
| 2013/0147604 A1 | 6/2013 | Jones et al. |
| 2013/0152139 A1 | 6/2013 | Davis et al. |
| 2013/0158717 A1 | 6/2013 | Zywicki et al. |
| 2013/0166073 A1 | 6/2013 | Pine et al. |
| 2013/0179926 A1 | 7/2013 | White et al. |
| 2013/0185750 A1* | 7/2013 | Ayoub .............. H04N 21/25841 725/34 |
| 2013/0204408 A1 | 8/2013 | Thiruvengada et al. |
| 2013/0219482 A1 | 8/2013 | Brandt |
| 2013/0238326 A1 | 9/2013 | Kim et al. |
| 2013/0242074 A1 | 9/2013 | Sekiguchi et al. |
| 2013/0247117 A1 | 9/2013 | Yamada et al. |
| 2013/0249688 A1 | 9/2013 | Nguyen et al. |
| 2013/0267383 A1 | 10/2013 | Watterson |
| 2013/0278828 A1 | 10/2013 | Todd |
| 2013/0289788 A1* | 10/2013 | Gupta ................... G05B 13/02 700/291 |
| 2013/0300576 A1 | 11/2013 | Sinsuan et al. |
| 2013/0318559 A1 | 11/2013 | Crabtree |
| 2013/0321637 A1 | 12/2013 | Frank et al. |
| 2013/0324247 A1 | 12/2013 | Esaki et al. |
| 2013/0325150 A1 | 12/2013 | Bury |
| 2014/0022051 A1 | 1/2014 | Levien et al. |
| 2014/0025798 A1 | 1/2014 | Apte et al. |
| 2014/0028546 A1 | 1/2014 | Jeon et al. |
| 2014/0070959 A1* | 3/2014 | Bhargava ................ H04Q 9/00 340/870.07 |
| 2014/0089671 A1 | 3/2014 | Logue et al. |
| 2014/0095684 A1 | 4/2014 | Nonaka et al. |
| 2014/0101465 A1 | 4/2014 | Wang et al. |
| 2014/0129006 A1 | 5/2014 | Chen et al. |
| 2014/0135993 A1 | 5/2014 | Kang et al. |
| 2014/0140575 A1 | 5/2014 | Wolf |
| 2014/0142724 A1 | 5/2014 | Park et al. |
| 2014/0160360 A1 | 6/2014 | Hsu et al. |
| 2014/0167969 A1 | 6/2014 | Wedig et al. |
| 2014/0168277 A1 | 6/2014 | Ashley et al. |
| 2014/0192197 A1 | 7/2014 | Hanko et al. |
| 2014/0192997 A1 | 7/2014 | Niu et al. |
| 2014/0201315 A1 | 7/2014 | Jacob et al. |
| 2014/0215505 A1 | 7/2014 | Balasubramanian et al. |
| 2014/0217905 A1 | 8/2014 | Clayton et al. |
| 2014/0218517 A1 | 8/2014 | Kim et al. |
| 2014/0222634 A1 | 8/2014 | Gordon et al. |
| 2014/0223548 A1 | 8/2014 | Wassingbo |
| 2014/0266669 A1 | 9/2014 | Fadell et al. |
| 2014/0266684 A1 | 9/2014 | Poder et al. |
| 2014/0282653 A1 | 9/2014 | Ariantaj et al. |
| 2014/0297001 A1 | 10/2014 | Silverman |
| 2014/0306833 A1 | 10/2014 | Ricci |
| 2014/0310075 A1 | 10/2014 | Ricci |
| 2014/0313014 A1 | 10/2014 | Huh et al. |
| 2014/0313032 A1 | 10/2014 | Sager et al. |
| 2014/0333529 A1 | 11/2014 | Kim et al. |
| 2014/0351832 A1 | 11/2014 | Cho et al. |
| 2014/0362201 A1 | 12/2014 | Nguyen et al. |
| 2014/0373074 A1 | 12/2014 | Hwang et al. |
| 2015/0008846 A1 | 1/2015 | Chen et al. |
| 2015/0015401 A1 | 1/2015 | Wedig et al. |
| 2015/0029096 A1 | 1/2015 | Ishihara |
| 2015/0054910 A1 | 2/2015 | Offen et al. |
| 2015/0061859 A1 | 3/2015 | Matsuoka et al. |
| 2015/0062343 A1 | 3/2015 | Hwang et al. |
| 2015/0066173 A1 | 3/2015 | Ellis et al. |
| 2015/0074259 A1 | 3/2015 | Ansari et al. |
| 2015/0082225 A1 | 3/2015 | Shearer |
| 2015/0084770 A1 | 3/2015 | Xiao et al. |
| 2015/0085184 A1 | 3/2015 | Vidal et al. |
| 2015/0097689 A1 | 4/2015 | Logue et al. |
| 2015/0100167 A1* | 4/2015 | Sloo ...................... G01N 27/02 700/278 |
| 2015/0105880 A1 | 4/2015 | Slupik et al. |
| 2015/0106866 A1 | 4/2015 | Fujita |
| 2015/0113571 A1 | 4/2015 | Cholas et al. |
| 2015/0116113 A1 | 4/2015 | Caine et al. |
| 2015/0127712 A1 | 5/2015 | Fadell et al. |
| 2015/0131500 A1 | 5/2015 | Xie et al. |
| 2015/0137967 A1 | 5/2015 | Wedig et al. |
| 2015/0142991 A1* | 5/2015 | Zaloom .................. H04L 43/10 709/248 |
| 2015/0143406 A1 | 5/2015 | Cho et al. |
| 2015/0143408 A1 | 5/2015 | Sallas |
| 2015/0145643 A1 | 5/2015 | Fadell et al. |
| 2015/0154850 A1 | 6/2015 | Fadell et al. |
| 2015/0156030 A1 | 6/2015 | Fadell et al. |
| 2015/0156612 A1 | 6/2015 | Vemulapalli |
| 2015/0159401 A1 | 6/2015 | Patrick et al. |
| 2015/0160623 A1 | 6/2015 | Holley |
| 2015/0160634 A1 | 6/2015 | Smith et al. |
| 2015/0160635 A1 | 6/2015 | Schofield et al. |
| 2015/0160636 A1 | 6/2015 | McCarthy et al. |
| 2015/0160663 A1* | 6/2015 | McCarthy, III ........ G05B 11/01 700/283 |
| 2015/0160935 A1 | 6/2015 | Nye |
| 2015/0161452 A1 | 6/2015 | McCarthy et al. |
| 2015/0161882 A1 | 6/2015 | Lett |
| 2015/0162006 A1 | 6/2015 | Kummer |
| 2015/0163411 A1 | 6/2015 | McCarthy, III et al. |
| 2015/0163412 A1 | 6/2015 | Holley et al. |
| 2015/0163535 A1 | 6/2015 | McCarthy et al. |
| 2015/0172742 A1 | 6/2015 | Richardson |
| 2015/0180708 A1 | 6/2015 | Jacob et al. |
| 2015/0192914 A1 | 7/2015 | Slupik |
| 2015/0198941 A1 | 7/2015 | Pederson |
| 2015/0241860 A1* | 8/2015 | Raid ..................... G05B 15/02 700/275 |
| 2015/0260424 A1 | 9/2015 | Fadell et al. |
| 2015/0281824 A1 | 10/2015 | Nguyen et al. |
| 2015/0309487 A1 | 10/2015 | Lyman |
| 2015/0325096 A1 | 11/2015 | Hatch |
| 2015/0334069 A1 | 11/2015 | Winston et al. |
| 2015/0341599 A1 | 11/2015 | Carey |
| 2015/0347910 A1 | 12/2015 | Fadell et al. |
| 2015/0365787 A1 | 12/2015 | Farrell |
| 2016/0029153 A1 | 1/2016 | Linn et al. |
| 2016/0041565 A1 | 2/2016 | Edwards |
| 2016/0047569 A1 | 2/2016 | Fadell et al. |
| 2016/0063854 A1 | 3/2016 | Burton et al. |
| 2016/0066046 A1 | 3/2016 | Mountain |
| 2016/0098309 A1 | 4/2016 | Kim |
| 2016/0100696 A1 | 4/2016 | Palashewski et al. |
| 2016/0109864 A1 | 4/2016 | Lonn |
| 2016/0121161 A1 | 5/2016 | Mountain |
| 2016/0123741 A1 | 5/2016 | Mountain |
| 2016/0163168 A1 | 6/2016 | Brav et al. |
| 2016/0182249 A1 | 6/2016 | Lea |
| 2016/0189527 A1 | 6/2016 | Peterson et al. |
| 2016/0191912 A1 | 6/2016 | Lea et al. |
| 2016/0191990 A1 | 6/2016 | McCarthy |
| 2016/0195856 A1 | 7/2016 | Spero |
| 2016/0196731 A1 | 7/2016 | Aich et al. |
| 2016/0203700 A1 | 7/2016 | Bruhn et al. |
| 2016/0234034 A1 | 8/2016 | Mahar et al. |
| 2016/0248598 A1 | 8/2016 | Lin et al. |
| 2016/0256485 A1* | 9/2016 | Wager .................... A61K 33/00 |
| 2016/0260135 A1 | 9/2016 | Zomet et al. |

(56) References Cited

U.S. PATENT DOCUMENTS

| | | |
|---|---|---|
| 2016/0285644 A1 | 9/2016 | Lu et al. |
| 2016/0286327 A1 | 9/2016 | Marten |
| 2016/0323548 A1 | 11/2016 | Khot et al. |
| 2016/0334811 A1 | 11/2016 | Marten |
| 2016/0335423 A1 | 11/2016 | Beals |
| 2016/0338179 A1 | 11/2016 | Aliakseyeu et al. |
| 2016/0342379 A1 | 11/2016 | Keipert et al. |
| 2016/0366746 A1 | 12/2016 | van de Ven et al. |
| 2017/0005822 A1 | 1/2017 | Gao |
| 2017/0041886 A1 | 2/2017 | Baker et al. |
| 2017/0048476 A1 | 2/2017 | Freiin von Kapri et al. |
| 2017/0051925 A1 | 2/2017 | Stefanski et al. |
| 2017/0054615 A1 | 2/2017 | Wilson |
| 2017/0065433 A1 | 3/2017 | Singh et al. |
| 2017/0082987 A1 | 3/2017 | Reddy et al. |
| 2017/0127124 A9 | 5/2017 | Wilson et al. |
| 2017/0146964 A1 | 5/2017 | Beals |
| 2017/0168469 A1 | 6/2017 | Marten et al. |
| 2017/0176961 A1 | 6/2017 | Tirpak |
| 2017/0187993 A1 | 6/2017 | Martch et al. |
| 2017/0191693 A1 | 7/2017 | Bruhn et al. |
| 2017/0191695 A1 | 7/2017 | Bruhn et al. |
| 2017/0195130 A1 | 7/2017 | Landow et al. |

FOREIGN PATENT DOCUMENTS

| | | |
|---|---|---|
| EP | 2 736 027 A1 | 5/2014 |
| EP | 3 080 677 A1 | 10/2016 |
| EP | 3 080 710 A1 | 10/2016 |
| GB | 2 304 952 A | 3/1997 |
| JP | 2008148016 A | 6/2008 |
| WO | 93/20544 A1 | 10/1993 |
| WO | 2004/068386 A1 | 8/2004 |
| WO | 2011/095567 A1 | 8/2011 |
| WO | 2011/149473 A1 | 12/2011 |
| WO | 2014/068556 A1 | 5/2014 |
| WO | 2015/179120 A1 | 11/2015 |
| WO | 2016/034880 A1 | 3/2016 |
| WO | 2016/066399 A1 | 5/2016 |
| WO | 2016/066442 A1 | 5/2016 |
| WO | 2016/182696 A1 | 11/2016 |
| WO | 2017/116533 A1 | 7/2017 |

OTHER PUBLICATIONS

Shunfeng Cheng et al., "A Wireless Sensor System for Prognostics and Health Management," IEEE Sensors Journal, IEEE Service Center, New York, NY, US, vol. 10, No. 4, Apr. 1, 2010, pp. 856-862, XP011304455, ISSN: 1530-437X, Sections 2 and 3.
International Search Report and Written Opinion for PCT/EP2015/070286 dated Nov. 5, 2015, 13 pages.
International Search Report and Written Opinion for PCT/GB2015/052544 dated Nov. 6, 2015, 10 pages.
U.S. Appl. No. 14/470,352, filed Aug. 27, 2014 Non Final Office Action dated Nov. 20, 2015, 28 pages.
International Search Report and Written Opinion for PCT/GB2015/052457 dated Nov. 13, 2015, 11 pages.
U.S. Appl. No. 12/700,310, filed Feb. 4, 2010 Final Office Action dated Oct. 26, 2015, 19 pages.
U.S. Appl. No. 14/107,132, filed Dec. 16, 2013, Final Rejection dated Dec. 16, 2015, 32 pages.
U.S. Appl. No. 12/700,310, filed Feb. 4, 2010 Notice of Allowance dated Nov. 8, 2014, 3 pages.
U.S. Appl. No. 14/567,765, filed Dec. 11, 2014, First Action interview dated Oct. 18, 2016, all pages.
U.S. Appl. No. 14/584,075, filed Dec. 29, 2014, Final Rejection dated Oct. 6, 2016, all pages.
U.S. Appl. No. 14/566,977, filed Dec. 11, 2014, Non Final Rejection dated Oct. 3, 2016, all pages.
U.S. Appl. No. 14/567,754, filed Dec. 11, 2014, Non Final Rejection dated Nov. 4, 2016, all pages.
U.S. Appl. No. 14/567,770, filed Dec. 11, 2014, Non Final Rejection dated Nov. 4, 2016, all pages.
U.S. Appl. No. 14/671,299, filed Mar. 27, 2015, Non Final Rejection dated Oct. 28, 2016, all pages.
U.S. Appl. No. 14/476,377, filed Sep. 3, 2014, Non-Final Rejection dated Nov. 7, 2016, all pages.
Office Action for EP14868928.4 dated Sep. 23, 2016, all pages.
U.S. Appl. No. 14/470,352, filed Aug. 27, 2014 Final Office Action dated Mar. 17, 2016, all pages.
U.S. Appl. No. 14/567,765, filed Dec. 11, 2014, Preinterview first office action dated Apr. 8, 2016, 30 pages.
U.S. Appl. No. 14/577,717, filed Dec. 19, 2014, Preinterview first office action dated Apr. 4, 2016, 29 pages.
U.S. Appl. No. 14/584,075, filed Dec. 29, 2014, Non-Final Rejection dated Apr. 1, 2016, 40 pages.
Mexican Institute of Industrial Property Office Action dated Nov. 1, 2013, for Mex. Patent Appln No. MX/a/2012/008882 is not translated into English, 3 pages.
Mexican Institute of Industrial Property Notice of Allowance dated Feb. 10, 2014, for Mex. Patent Appln No. MX/a/2012/008882, 1 page.
Wang et al., "Mixed Sound Event Verification on Wireless Sensor Network for Home Automation," IEEE Transactions on Industrial Informatics, vol. 10, No. 1, Feb. 2014, 10 pages.
U.S. Appl. No. 12/700,310, filed Feb. 4, 2010 Non-Final Office Action dated Mar. 11, 2015, 35 pages.
U.S. Appl. No. 14/470,352, filed Aug. 27, 2014 Non Final Office Action dated Aug. 26, 2016, all pages.
U.S. Appl. No. 14/107,132, filed Dec. 16, 2013, Non Final Office Action dated Jul. 18, 2016, all pages.
U.S. Appl. No. 14/715,248, filed May 18, 2015, Non-Final Rejection dated Jul. 19, 2016, 34 pages.
U.S. Appl. No. 14/567,783, filed Dec. 11, 2014, Non Final Rejection dated Aug. 23, 2016, all pages.
International Search Report and Written Opinion for PCT/US2016/028126 dated Jun. 3, 2016, all pages.
U.S. Appl. No. 12/700,310, filed Feb. 4, 2010 Non-Final Office Action dated Jun. 16, 2016, 30 pages.
U.S. Appl. No. 14/528,739, filed Oct. 30, 2014 Notice of Allowance dated Jun. 23, 2016, 34 pages.
U.S. Appl. No. 14/485,188, filed Sep. 12, 2014, Non-Final Rejection dated Jun. 17, 2016, 29 pages.
U.S. Appl. No. 14/710,331, filed May 12, 2015, Non-Final Rejection dated May 20, 2016, 42 pages.
International Preliminary Report on Patentability for PCT/US2014/055441 dated Jun. 14, 2016, 8 pages.
International Preliminary Report on Patentability for PCT/US2014/053876 dated Jun. 14, 2016, 7 pages.
International Preliminary Report on Patentability for PCT/US2014/055476 dated Jun. 14, 2016, 9 pages.
U.S. Appl. No. 14/485,188, filed Sep. 12, 2014, Pre-Interview First Office Action dated Jul. 29, 2015, 20 pages.
U.S. Appl. No. 14/485,188, filed Sep. 12, 2014, Pre-Interview First Office Action date dOct. 1, 2015, 10 pages.
U.S. Appl. No. 14/107,132, filed Dec. 16, 2013 Non Final Office Action dated May 27, 2015, 26 pages.
"Acoustic/Ultrasound Ultrasonic Flowmeter Basics," Questex Media Group LLC, accessed on Dec. 16, 2014, 4 pages. Retrieved from http://www.sensorsmag.com/sensors/acoustic-ultrasound/ultrasonic-flowmeter-basics-842.
"AllJoyn Onboarding Service Frameworks," Qualcomm Connected Experiences, Inc., accessed on Jul. 15, 2014, 9 pages. Retrieved from https://www.alljoyn.org.
"App for Samsung Smart TV®," Crestron Electronics, Inc., accessed on Jul. 14, 2014, 3 pages. Retrieved from http://www.crestron.com/products/smart tv television apps/.
"Do you want to know how to find water leaks? Use a Bravedo Water Alert Flow Monitor to find out!", Bravedo.com, accessed Dec. 16, 2014, 10 pages. Retrieved from http://bravedo.com/.
"Flow Pulse®, Non-invasive clamp-on flow monitor for pipes," Pulsar Process Measurement Ltd, accessed on Dec. 16, 2014, 2 pages. Retrieved from http://www.pulsar-pm.com/product-types/flow/flow-pulse.aspx.

(56) References Cited

OTHER PUBLICATIONS

"International Building Code Excerpts, Updated with recent code changes that impact electromagnetic locks," Securitron, Assa Abloy, IBC/IFC 2007 Supplement and 2009, "Finally-some relief and clarification", 2 pages. Retrieved from: www.securitron.com/Other/.../New_IBC-IFC_Code_Language.pdf.
"Introduction to Ultrasonic Doppler Flowmeters," OMEGA Engineering inc., accessed on Dec. 16, 2014, 3 pages. Retrieved from http://www.omega.com/prodinfo/ultrasonicflowmeters.html.
"Ultrasonic Flow Meters," RS Hydro Ltd, accessed on Dec. 16, 2014, 3 pages. Retrieved from http://www.rshydro.co.uk/ultrasonic-flowmeter.shtml.
"Voice Activated TV using the Amulet Remote for Media Center," AmuletDevices.com, accessed on Jul. 14, 2014, 1 page. Retrieved from http://www.amuletdevices.com/index.php/Features/television.html.
International Search Report and Written Opinion for PCT/US2014/055476 dated Dec. 30, 2014, 10 pages.
International Search Report and Written Opinion of PCT/EP2011/051608 dated May 30, 2011, 13 pages.
International Preliminary Report on Patentability for PCT/EP2011/051608 dated Aug. 16, 2012, 8 pages.
International Search Report and Written Opinion of PCT/US2014/053876 dated Nov. 26, 2014, 8 pages.
Lamonica, M., "CES 2010 Preview: Green comes in many colors," retrieved from CNET.com (http://ces.cnet.com/8301-31045_1-10420381-269.html), Dec. 22, 2009, 2 pages.
Mexican Institute of Industrial Property Office Action dated Dec. 16, 2013, for Mex. Patent Appln No. MX/a/2012/008882, 3 pages.
Robbins, Gordon, Deputy Chief, "Addison Fire Department Access Control Installation," 2006 International Fire Code, Section 1008.1.3.4, 4 pages.
U.S. Appl. No. 12/700,310, filed Feb. 4, 2010 Non-Final Office Action dated Aug. 14, 2014, 18 pages.
U.S. Appl. No. 12/700,310, filed Feb. 4, 2010 Final Office Action dated Feb. 28, 2014, 17 pages.
U.S. Appl. No. 12/700,310, filed Feb. 4, 2010 Non-Final Office Action dated Oct. 15, 2013, 15 pages.
U.S. Appl. No. 12/700,310, filed Feb. 4, 2010 Non-Final Office Action dated Apr. 1, 2013, 16 pages.
U.S. Appl. No. 12/700,310, filed Feb. 4, 2010, Final Office Action dated Oct. 10, 2012, 16 pages.
U.S. Appl. No. 12/700,310, filed Feb. 4, 2010, Office Action dated May 4, 2012, 15 pages.
U.S. Appl. No. 12/700,408, filed Feb. 4, 2010, Notice of Allowance dated Jul. 28, 2012, 8 pages.
U.S. Appl. No. 13/680,934, filed Nov. 19, 2012, Notice of Allowance dated Jul. 25, 2014, 12 pages.
U.S. Appl. No. 13/680,934, filed Nov. 19, 2012, Notice of Allowance dated Apr. 30, 2014, 9 pages.
U.S. Appl. No. 13/680,934, filed Nov. 19, 2012, Final Office Action dated Feb. 10, 2014, 13 pages.
U.S. Appl. No. 13/680,934, filed Nov. 19, 2012, Non-Final Office Action dated Oct. 2, 2013, 7 pages.
International Search Report and Written Opinion for PCT/EP2015/073299 dated Jan. 4, 2016, 12 pages.
International Search Report and Written Opinion for PCT/EP2015/073936 dated Feb. 4, 2016, all pages.
U.S. Appl. No. 14/485,188, filed Sep. 12, 2014, Final Rejection dated Feb. 23, 2016, 22 pages.
U.S. Appl. No. 14/567,348, filed Dec. 11, 2014, Preinterview first office action dated Jan. 20, 2016, 23 pages.
U.S. Appl. No. 14/470,352, filed Aug. 27, 2014 Notice of Allowance dated Dec. 2, 2016, all pages.
U.S. Appl. No. 15/050,958, filed Feb. 23, 2016 Notice of Allowance dated Dec. 6, 2016, all pages.
U.S. Appl. No. 15/289,395, filed Oct. 10, 2016 Non-Final Rejection dated Dec. 2, 2016, all pages.
U.S. Appl. No. 14/485,188, filed Sep. 12, 2014, Final Rejection dated Nov. 25, 2016, 22 pages.
U.S. Appl. No. 14/577,717, filed Dec. 19, 2014, Final Office Action dated Dec. 19, 2016, all pages.
U.S. Appl. No. 14/567,783, filed Dec. 11, 2014, Final Rejection dated Dec. 20, 2016, all pages.
U.S. Appl. No. 15/075,412, filed Mar. 21, 2016, Non Final Rejection dated Dec. 21, 2016, all pages.
International Preliminary Report on Patentability for PCT/GB2015/052544 dated Mar. 7, 2017, all pages.
Notification of Publication of European Application No. 162004220 as EP 3166308 on May 10, 2017, 2 pages.
U.S. Appl. No. 14/485,188, filed Sep. 12, 2014, Non-Final Rejection dated Apr. 19, 2017, all pages.
U.S. Appl. No. 14/671,299, filed Mar. 27, 2015, Notice of Allowance dated Apr. 17, 2017, all pages.
U.S. Appl. No. 15/075,412, filed Mar. 21, 2016, Final Rejection dated Apr. 17, 2017, all pages.
U.S. Appl. No. 14/528,402, filed Oct. 30, 2014, Non-Final Rejection dated Apr. 11, 2017, all pages.
U.S. Appl. No. 14/475,252, filed Sep. 2, 2014, Non-Final Rejection dated Apr. 12, 2017, all pages.
U.S. Appl. No. 14/832,821, filed Aug. 21, 2015, Non-Final Rejection dated Apr. 24, 2017, all pages.
U.S. Appl. No. 14/981,501, filed Dec. 28, 2015, Preinterview first office action dated Apr. 20, 2017, all pages.
U.S. Appl. No. 14/567,765, filed Dec. 11, 2014, Notice of Allowance dated May 24, 2017, all pages.
U.S. Appl. No. 14/567,754, filed Dec. 11, 2014, Final Rejection dated May 26, 2017, all pages.
U.S. Appl. No. 14/567,770, filed Dec. 11, 2014, Final Rejection dated Jun. 1, 2017, all pages.
U.S. Appl. No. 14/476,377, filed Sep. 3, 2014, Notice of Allowance dated May 19, 2017, all pages.
U.S. Appl. No. 14/709,791, filed May 12, 2015, Non Final Rejection dated May 31, 2017, all pages.
Bdejong_Cree, "Cannot remove last user of a group even though members still exist," Microsoft Visual Studio forum site, Topic ID #58405, Response by Microsoft, Dec. 17, 2010) retrieved on Apr. 6, 2017 from: https://connect.microsoft.com/VisualStudio/feedback/details/580405/tfs-2010-cannot-remove-last-user-of-a-group-even-though-members-still-exists.
International Search Report and Written Opinion for PCT/US2016/057729 dated Mar. 28, 2017, all pages.
European Search Report for EP 16 20 0422 dated Jan. 13, 2017, all pages.
International Preliminary Report on Patentability for PCT/GB2015/052457 dated Feb. 28, 2017, all pages.
U.S. Appl. No. 14/107,132, filed Dec. 16, 2013, Notice of Allowance dated Jan. 18, 2017, all pages.
U.S. Appl. No. 14/567,765, filed Dec. 11, 2014, Final Rejection dated Feb. 16, 2017, all pages.
U.S. Appl. No. 14/485,038, filed Sep. 12, 2014, Non Final Rejection dated Apr. 6, 2017, all pages.
U.S. Appl. No. 14/584,075, filed Dec. 29, 2014, Non-Final Rejection dated Mar. 10, 2017, all pages.
U.S. Appl. No. 14/710,331, filed May 12, 2015, Non-Final Rejection dated Mar. 10, 2017, all pages.
U.S. Appl. No. 14/566,977, filed Dec. 11, 2014, Final Rejection dated Feb. 10, 2017, all pages.
U.S. Appl. No. 14/565,853, filed Dec. 10, 2014, Non Final Rejection dated Mar. 10, 2017, all pages.
U.S. Appl. No. 15/289,395, filed Oct. 10, 2016 Non-Final Rejection dated Jun. 19, 2017, all pages.
U.S. Appl. No. 14/981,501, filed Dec. 28, 2015, First Action Interview—office action dated Jul. 19, 2017, all pages.
International Preliminary Report on Patentability for PCT/US2016/028126 dated Nov. 14, 2017, all pages.
International Search Report and Written Opinion for PCT/US2017/047900 dated Nov. 24, 2017.
Ravindran, et al., "Information-centric Networking based Homenet," 2013 IFIP/IEEE International Symposium on Integrated Network Management (IM 2013), Ghent, 2013, pp. 1102-1108.

(56) References Cited

OTHER PUBLICATIONS

Mantoro, et al., "Web-enabled Smart Home Using Wireless Node Infrastructure," Proceedings of the 9th International Conference on Advances in Mobile Computing and Multimedia. ACM, 2011, pp. 72-79.

Shariqsuhail, et al., "Multi-Functional Secured Smart Home," Advances in Computing, Communications and Informatics (ICACCI), 2016 International Conference on. IEEE, 2016, pp. 2629-2634.

U.S. Appl. No. 14/986,483, filed Dec. 31, 2015, Non-Final Rejection dated Dec. 1, 2017, all pages.

U.S. Appl. No. 14/584,075, filed Dec. 29, 2014, Notice of Allowance dated Dec. 26, 2017, all pages.

U.S. Appl. No. 14/710,331, filed May 12, 2015, Notice of Allowance dated Dec. 7, 2017, all pages.

U.S. Appl. No. 14/832,821, filed Aug. 21, 2015, Notice of Allowance dated Dec. 18, 2017, all pages.

Notification of Publication of European Application No. 15763643.2 as EP 3189511 on Jul. 12, 2017, 1 page.

Notification of Publication of Brazilian Application No. BR 11 2016 0112032 dated Aug. 8, 2017, 2 pages.

Notification of Publication of Brazilian Application No. BR 11 2016 010376 9 dated Aug. 8, 2017, 1 page.

Supplementary European Search Report for EP 14868928 dated Jul. 7, 2017, 11 pages.

Supplementary European Search Report for EP 14870507 dated Jun. 28, 2017, all pages.

"Plug-In Carbon Monoxide & Natural Gas Alarm with Backup Battery Protection," Universal Security Instruments, Inc., 2011, 12 pages.

Mark Edward Soper, "Absolute Beginner's Guide to Home Automation," 2005, Que Publishing, p. 57, 121.

U.S. Appl. No. 14/553,763, filed Nov. 25, 2014 Preinterview first office action dated Oct. 6, 2017, all pages.

U.S. Appl. No. 14/584,075, filed Dec. 29, 2014, Final Rejection dated Sep. 9, 2017, all pages.

U.S. Appl. No. 14/952,580, filed Nov. 25, 2015, Non-Final Rejection dated Sep. 20, 2017, all pages.

U.S. Appl. No. 15/189,775, filed Jun. 22, 2016, Notice of Allowance dated Sep. 11, 2017, all pages.

U.S. Appl. No. 14/986,496, filed Dec. 31, 2015, Non-Final Rejection dated Sep. 26, 2017, all pages.

U.S. Appl. No. 14/710,331, filed May 12, 2015, Final Rejection dated Aug. 16, 2017, all pages.

U.S. Appl. No. 14/981,501, filed Dec. 28, 2015, Final Office Action dated Oct. 10, 2017, all pages.

U.S. Appl. No. 14/567,502, filed Dec. 11, 2014, Final Rejection dated Aug. 7, 2017, all pages.

U.S. Appl. No. 14/982,366, filed Dec. 29, 2015, Non-Final Rejection dated Nov. 1, 2017, all pages.

U.S. Appl. No. 15/246,079, filed Aug. 24, 2016, Non-Final Rejection dated Oct. 19, 2017, all pages.

U.S. Appl. No. 14/485,188, filed Sep. 12, 2014, Final Rejection dated Oct. 25, 2017, all pages.

U.S. Appl. No. 14/485,038, filed Sep. 12, 2014, Notice of Allowance dated Nov. 13, 2017, all pages.

U.S. Appl. No. 14/528,402, filed Oct. 30, 2014, Final Rejection dated Oct. 31, 2017, all pages.

\* cited by examiner

DETECTION AND PREVENTION OF TOXIC GAS

BACKGROUND OF THE INVENTION

Control and monitoring systems for homes are typically designed for a limited and specific function. The specificity often limits the systems' flexibility and usability. Home monitoring is often limited to specific tasks with limited diagnostics and mitigations functions. Current systems for detecting toxic gases, such as carbon monoxide, only provide detection and are not able to provide functions for diagnostics or mitigation. Many toxic gases may be colorless and odorless and may emanate under limited circumstances making diagnosis of the cause of the gases difficult or impossible using existing systems.

BRIEF SUMMARY OF THE INVENTION

In some embodiments a method for automation control for carbon monoxide diagnosis is presented. The method includes receiving carbon monoxide sensor readings from one or more carbon monoxide detectors and recording carbon monoxide sensor readings over a first time period. The method also includes monitoring activity of components of a home over the first time period. The activity of components may be at least in part based on a first activity schedule and constrained by a user input. The method may further include identifying a first correlation between the activity of components of the home and the carbon monoxide sensor readings over the first time period and generating a second activity schedule for a second time period. The second activity schedule may be configured to meet user constraints and test the first correlation between the activity and the carbon monoxide sensor readings. In embodiments, the method may also include recording carbon monoxide sensor readings over the second time period, monitoring activity of components of the home over the second time period, and identifying a second correlation between the activity of components and the carbon monoxide sensor readings over the second time period. The method may also include determining if the first correlation and the second correlation are consistent.

In some embodiments the method may also include monitoring readings of home sensors in the home, determining activity of home appliances based on readings of the home sensors, and determining a third correlation between the home sensor readings and carbon monoxide sensor readings. In some cases a ventilation system may be activated when carbon monoxide readings exceed a threshold. In some cases if the first correlation and the second correlation is consistent a report may be provided to a user. In some embodiments the second activity schedule may be configured to change the activity of components from the first activity schedule of the home that were correlated to the carbon monoxide sensor readings. In some embodiments the second activity schedule may be configured to change relative timing of the activity of components from the first activity schedule.

In some embodiments a non-transitory processor-readable medium for automation control for carbon monoxide diagnosis is presented. The medium may include processor-readable instructions configured to cause one or more processors to receive carbon monoxide sensor readings from one or more carbon monoxide detectors, record carbon monoxide sensor readings over a first time period, and monitor activity of components of a home over the first time period. The activity of components may be at least in part based on a first activity schedule and constrained by a user input. The instruction may be further configured to identify a first correlation between the activity of components of the home and the carbon monoxide sensor readings over the first time period and generate a second activity schedule for a second time period. The second activity schedule may be configured to meet user constraints and test the first correlation between the activity and the carbon monoxide sensor readings. The instructions may be further configured to record carbon monoxide sensor readings over the second time period, monitor activity of components of the home over the second time period, identify a second correlation between the activity of components and the carbon monoxide sensor readings over the second time period, and determine if the first correlation and the second correlation are consistent.

In some embodiments a television receiver configured for automation control for carbon monoxide diagnosis is presented. The television receiver may include one or more processors and a memory communicatively coupled with and readable by the one or more processors and having stored therein processor-readable instructions which, when executed by the one or more processors, cause the one or more processors to receive carbon monoxide sensor readings from one or more carbon monoxide detectors and record carbon monoxide sensor readings over a first time period. The activity of components of a home may be monitored over the first time period. The activity of components may be at least in part based on a first activity schedule and constrained by a user input. The instructions may cause the one or more processors to identify a first correlation between the activity of components of the home and the carbon monoxide sensor readings over the first time period and generate a second activity schedule for a second time period. The second activity schedule may be configured to meet user constraints and test the first correlation between the activity and the carbon monoxide sensor readings. The instructions may cause the one or more processors to further record carbon monoxide sensor readings over the second time period, monitor activity of components of the home over the second time period, and identify a second correlation between the activity of components and the carbon monoxide sensor readings over the second time period. In some embodiments, instructions may cause the one or more processors to also determine if the first correlation and the second correlation are consistent.

BRIEF DESCRIPTION OF THE DRAWINGS

A further understanding of the nature and advantages of various embodiments may be realized by reference to the following figures. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION OF THE INVENTION

Figure 1:
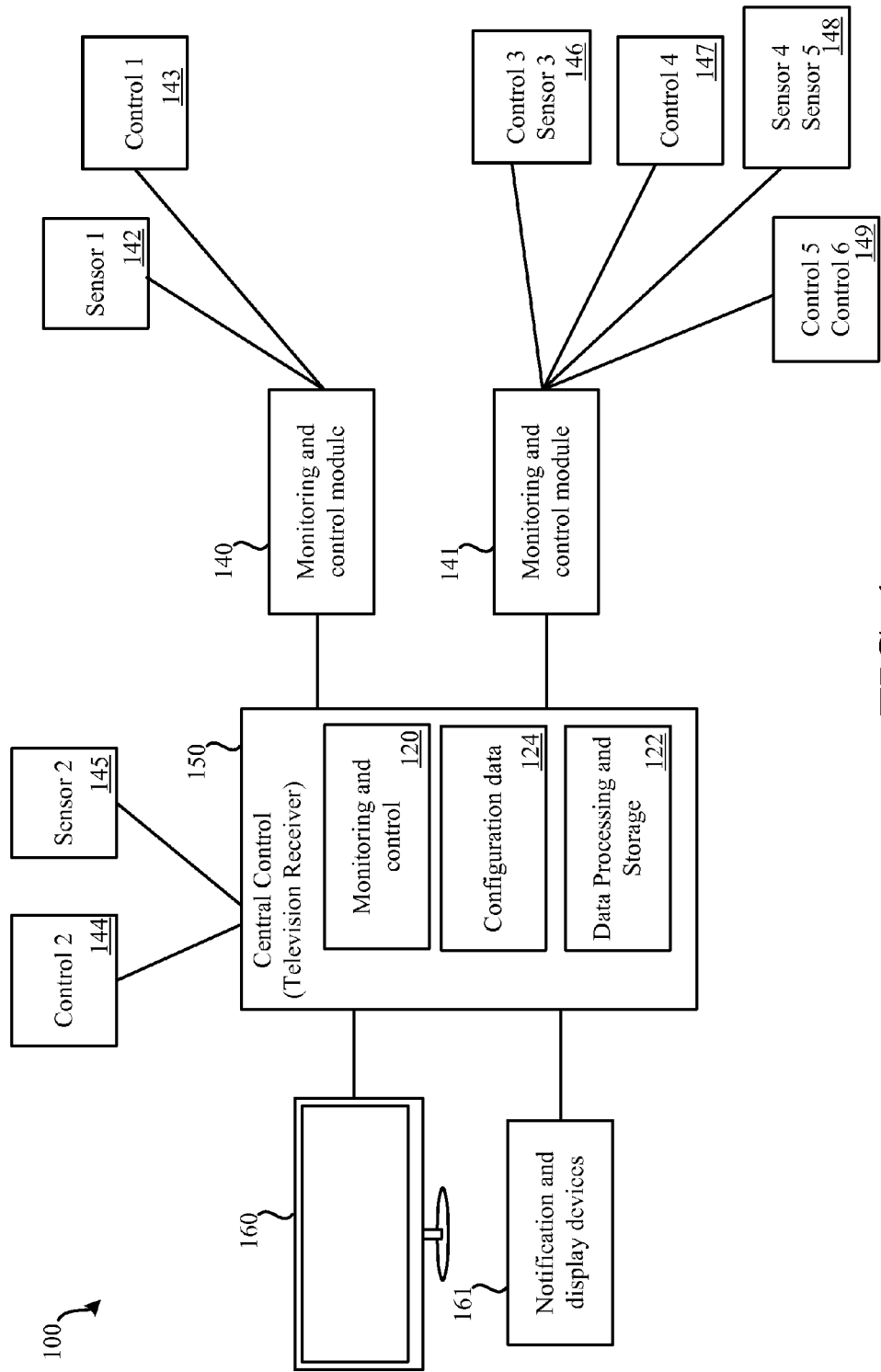
FIG. 1 illustrates an embodiment of a home monitoring and control system.

Toxic or dangerous gases such as carbon monoxide, carbon dioxide, natural gas, sewer gases, and the like may build up in a home. Some gases may originate from house hold systems such as home furnaces, fireplaces, heaters, septic system, and the like. Some gases, such as carbon monoxide, for example are completely colorless and odorless making their presence difficult to detect by a person.

In some cases the cause or source of a toxic gas may be difficult to diagnose. Toxic gas emanations may depend on a variety of factors that may be very difficult to detect or diagnose. Toxic gases may only be present during the operation of a specific component. In some cases the activity of a first component may cause a second component in a home to malfunction thereby causing buildup of toxic gases. The activity of the first component activity coinciding with the activity of a second component may rarely occur thereby complicating diagnosis. In some cases the emanations of toxic gases may depend on environmental factors such as wind conditions, weather, humidity, temperature, or a combination thereof.

For example, the activity of a gas clothes dryer at the same time as a gas furnace may result in carbon monoxide buildup. In one configuration, both the gas dryer and furnace may use the same exhaust duct. The exhaust duct may be too small to accommodate the exhaust of both the dryer and the furnace operating simultaneously. When both the dryer and the furnace are active at the same time excessive exhaust gas pressure in the duct may cause blow back of gasses into the home causing carbon monoxide buildup.

In another example, carbon monoxide may build up in a home due to wind conditions. Windy conditions may cause a ventilation valve used to control furnace exhaust gases to malfunction. Wind may prevent a ventilation flap on the outside of a home from fully opening causing the buildup of toxic gases.

In embodiments, components of a home automation system may include gas detectors. Detectors for carbon monoxide, carbon dioxide, natural gas, and the like may be used to measure levels of a toxic gas in a home. Readings from the detectors/sensors may be collected by a central controller in a home. The central controller may receive readings from other home automation components and/or may be configured to control other home automation components.

A central controller may monitor and record sensor readings and activity of components of a home. The central controller may identify time periods with elevated, unusual, or dangerous levels of toxic gases. The central controller may analyze the activity of components of a home, sensor readings of a home, and/or environmental conditions to determine dependencies or correlations. The central controller may compare or correlate readings of elevated or unhealthy levels of gases with the activity of other components of a home. The central controller may identify possible causes of elevated gases based on the correlations.

For example, a central controller may monitor toxic gas readings and the activity of a home furnace. The periods of time when the furnace if active may be compared to periods of time when elevated or unusual gas readings are observed. The overlap between the active time periods of the furnace and elevated sensor readings may be analyzed. When more than 50% or more of the time periods coincide, the central controller may flag the furnace as a potential source of gas emissions. In embodiments, the central controller may use any number of correlation functions, statistical analysis, or the like to identify similarities or cause of elevates sensor readings.

In some cases the correlations between activity of components and gas sensor readings may be inconclusive. In some cases activity or two or more components may be correlated or related with elevated toxic gas levels. In some embodiments, the central controller may modify the activity of components to determine or clarify a correlation between activity of components and elevated gas readings. A central controller may change the relative timing of the activity of two or more components. The duration of activity, the frequency of activity, and the like may be altered to identify a correlation or dependency.

For example, during the monitoring of component activity and sensor readings, the central controller may determine that the activity of two or more components may be correlated to the measured toxic gas levels. The central controller may modify the activity schedule of the components to determine if only one of the components is causing elevated gas levels, or if it is the interaction of two or more components. The central controller may change the relative timing of the activity of the components monitor the toxic gas readings. Correlations between the activity based on the new activity schedule may be compared to the first identified correlations. Multiple modifications or iterations of modification of the activity schedules may be necessary to pinpoint possible causes of toxic gases. Modifications of activity schedule may be designed to test specific hypothesis of causality. The relative timing of activity may be configured to test causality between components.

The modification of the activity schedule of components may be constrained by user settings or user activity. The change in activity timing may be constrained by specific user settings. For example, the activity of a furnace in the winter may be constrained by a user's thermostat setting. The timing of the activity of the furnace may be changed provided the temperature settings specified by the user are met. In another example, user activity such as water usage may constrain the use of a water heater.

In embodiments the central controller may be configured to diagnose the source of toxic gas and/or initiate a mitigation plan or action to reduce gas buildup or the exposure of the gas to a user. A central controller may activate systems such as a ventilation system or open windows. In some cases the central controller may activate a mitigation system to direct airflow to minimize toxic gas exposure in the areas of a home where a user is present.

In some embodiments, some components of a home may not be automated or controlled by a central controller of a home automation system. In some cases, the central controller may use other sensors to monitor the activity of the component. In some cases the activity of the component may be modified by changing the activity of other components.

For example, in some systems a furnace of a home may not be connected to a central controller of a home automation system. To monitor the activity of the furnace, the central controller may monitor the temperature of the home and infer the activity of the furnace. Based on changes of temperature, such as a rise in temperature, may be identified as the result of the furnace heating the home. Additional temperature sensors such as outside temperature sensors may be used to identify causes of natural temperature changes and those caused by furnace activity. The activity of the furnace may be modified or indirectly controlled by a central controller by, for example, activating ventilation or opening windows. The ambient temperature of the interior of the home may be altered to activate the furnace despite that the central control does not have direct control of the furnace.

In embodiments, the central controller of a home automation system may monitor gas sensor readings to determine a baseline reading. The toxic gas sensors may be monitored to identify deviation from the baseline. Deviations from the baseline may trigger the controller to initiate a diagnostic mode that may find correlations between changes in the baseline to component activity. The central control may cause changes in the activity of system components to test causality. Monitoring the baseline and triggering a diagnostic mode based on changes to the baseline may allow the system to identify emerging problems in components before they become dangerous to the occupants of the home.

A central controller in a home may provide for a control interface to view correlation analysis and the identified possible causes or elevated toxic gas readings. In some embodiments, the central controller may be a television receiver. The television receiver may be communicatively coupled to receive readings from one or more components that may be sensors or control modules of the system.

Television receivers such as set-top boxes, satellite based television systems, and/or the like are often centrally located within a home. Television receivers are often interconnected to remote service providers, have wired or wireless interconnectivity with mobile devices, provide a familiar interface and are associated or connected with a large display that may be used displaying status and control functions.

Television receivers may be configured to receive information from sensors, telemetry equipment, and other systems in a home. Capabilities of the television receivers may be utilized to analyze sensor and telemetry readings, receive user input or configurations, provide visual representations and analysis of sensor readings and the like. For example, the processing and data storage capabilities of the television receivers may be used to analyze and process sensor readings. The sensor readings may be stored on the data storage of the receiver providing historical data for analysis and interpretation.

Capabilities of the television receiver may be configured to provide an intuitive and adaptable interface and platform for deploying and configuring control and monitoring systems and/or functionality. Televisions and or other display devices, such as smart phones, tablets, and the like provide a familiar and adaptable interface for users in a centrally located location of the home. Sensors, controls, and the like may be used for more than one control and monitoring function. Applications, monitoring functions, control functions may be selected and configured on the television receiver to perform different types of control and monitoring tasks using one or more sensors or control devices.

FIG. 1 shows an embodiment of a system for home monitoring and control that includes a television receiver 150. The system 100, may include a television receiver that is directly or indirectly coupled to one or more display devices 160 such as a television or a monitor. The television receiver may be communicatively coupled to other display and notification devices 161 such stereo systems, speakers, lights, mobile phones, tablets, and the like. The television receiver may be configured to receive readings from one or more sensors 145, 142, or sensor systems 148 and may be configured to provide signals for controlling one or more control units 144, 143, 147 or control systems 149.

In embodiments the television receiver may include a monitoring and control module 120 and may be directly connected or coupled to one or more sensors 145 and/or control units 144. Sensors and control units may be wired or wirelessly coupled to the television receiver. The sensors and control units may be coupled and connected in a serial, parallel, star, hierarchical, and/or the like topologies and may communicate to the television receiver via one or more serial, bus, or wireless protocols and technologies which may include, for example, WiFi, CAN bus, Bluetooth, I2C bus, ZigBee, Z-Wave, Homeplug, MOCA, and/or the like.

In some embodiments, the system may include one or more monitoring and control modules 140, 141 that are external to the television receiver 150. In embodiments the television receiver may interface to sensors and control units via one or more monitoring and control modules 140, 141. The external monitoring and control modules 140, 141 may be wired or wirelessly coupled to the television receiver. In some embodiments the monitoring and control modules 140, 141 may connect to the television receiver 150 via a communication port such as a USB port, serial port, and/or the like. In some embodiments the monitoring and control modules 140, 141 may connect to the television receiver via a wireless communication protocol such as Wi-Fi, Bluetooth, Z-Wave, ZigBee, and the like. The external monitoring and control modules may a separate device that may be positioned near the television receiver or may be in a different location, remote from the television receiver.

Monitoring and control modules 120, 140, 141 may be coupled to components such as sensors. Sensors may include any number of temperate, humidity, sound, proximity, field, electromagnetic, magnetic sensors, cameras, infrared detectors, motion sensors, pressure sensors, smoke sensors, fire sensors, water sensors, carbon monoxide sensors, and/or the like.

Monitoring and control modules 120, 140, 141 may be coupled components such as control units. Control units may include any number of switches, solenoids, solid state devices and/or the like for making noise, bells/alarms, turning on/off electronics, heating and cooling elements, controlling appliances, HVAC systems, lights, and/or the like. For example, a control unit may be a device that plugs in to an electrical outlet of a home. Other devices, such as an appliance, may be plugged into the device. The device may be controlled remotely to enable or disable electricity to flow to the appliance.

Sensors may be part of other devices and/or systems. For example, sensors may be part of a mobile device such as a phone. The telemetry readings of the sensors may be accessed through a wireless communication interface such as a Bluetooth connection from the phone. As another example, temperature sensors may be part of a heating and ventilation system of a home. The readings of the sensors may be accessed via a communication interface of the heating and ventilation system.

Control units may be part of other devices and/or systems. A control unit may be part of an appliance, heating or cooling system, and/or other electric or electronic device. In embodiments the control units of other system may be controlled via a communication or control interface of the system. For example, the water heater temperature setting may be configurable and/or controlled via a communication interface of the water heater or home furnace.

Sensors and/or control units may be combined into assemblies or units with multiple sensing capabilities and/or control capabilities. A single module may include, for example a temperature sensor and humidity sensor. Another module may include a light sensor and power or control unit and so on.

During operation of the system 100, readings from the sensors may be collected, stored, and/or analyzed in the television receiver 150. In embodiments, analysis of the sensors and control of the control units may be determined by a configuration data 124 stored in the television receiver 150. The configuration data may define how the sensor data is collected, how often, what periods of time, what accuracy is required, and other characteristics. The configuration data may specify specific sensor and/or control unit settings for a monitoring and/or control application. The configuration data may define how the sensor readings are processed and/or analyzed. For example, for some applications, sensor analysis may include collecting sensor readings and performing time based analysis to determine trends. For other applications, sensor analysis may include monitoring sensor readings to determine if a threshold value of one or more sensor has been reached.

The function of the system may be determined by loading and/or identifying configuration data for an application. In embodiments, the system 100 may be configured for more than one monitoring or control operation by selecting or loading the appropriate configuration data. Configuration data may define monitoring operations, reactive measures, activation constraints for components of the system, and the like.

In embodiments the system may include additional notification and display devices 161 capable of notifying the user, showing the status, configuration data, and/or the like. The additional notification and display devices may be devices that directly or indirectly connected to the television receiver. In some embodiments computers, mobile devices, phones, tablets, and the like may receive information, notifications, from the television receiver. Data related to the toxic gas readings or identified causes may be transmitted to remote devices and displayed to a user.

Readings processed by the monitoring and control modules 120, 140, 141 may be logged and analyzed by the data processing and storage module 122. The data processing and storage 122 module may analyze the received data and generate control signals, schedules, and/or sequences for controlling components. The data processing and storage module 122 may for example receive sensor data from toxic gas sensors such as carbon monoxide sensors. The data may be monitored and recorded over a time period. Over the same time period the data processing and storage module 122 may record the activity of components of the system and may determine correlations between the sensor readings and the activity of the components. Based at least in part on the sensor readings, the data processing and storage module may cause the system to activate one or more components to mitigate gas exposure or test the correlations.

Figure 2:
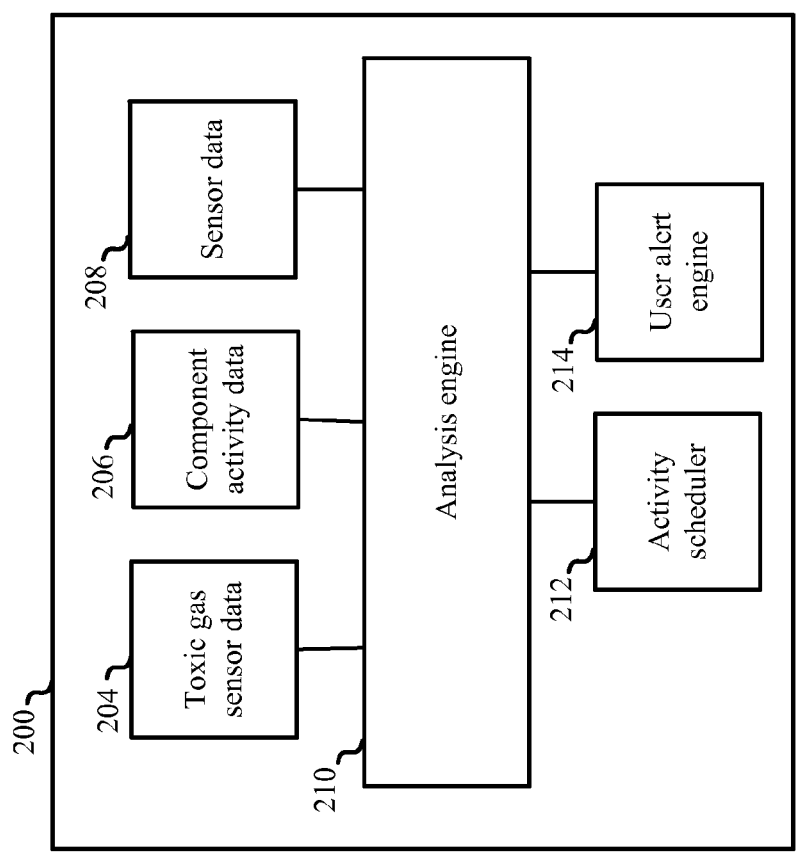
FIG. 2 illustrates an embodiment of a data processing and storage module.

FIG. 2 illustrates an embodiment of a data processing and storage module 200 configured for processing readings from toxic gas sensors and analyzing the readings to determine possible causes of elevated readings. Data processing and storage module 200 represents an embodiment of the data processing and storage module 122 of FIG. 1. The module 200 is illustrated as being composed of multiple components. It should be understood that the module 200 may be broken into a greater number of components or collapsed into fewer components. Each component of the module 200 may include computerized hardware, software, and/or firmware. In some embodiments, the module may be implemented as software that is executed by a processor the central control 150 of FIG. 1. Data processing and storage 200 may include an analysis engine 210, toxic gas sensor data 204, component activity data 206, and other sensor data 208. The module 200 may also include an analysis engine 210, an activity scheduler 212, and a user alert engine 214.

The module 200 may analyze gas sensor data to determine toxic gas levels and correlations using the analysis engine 210. The analysis engine may access gas sensor data 204 such carbon monoxide sensor readings from sensors located around a home. The sensor data may be associated with locations in the home. The analysis engine may access component activity data 206. Component activity data may include on and off times for various components. Component activity data may be obtained by directly monitoring the activity of components. In some cases an activity schedule may be received that includes the activity of the components. The component activity data 206 may include activity constraints for the components. The constraints may be set be a user, for example, such as temperature settings. The constraints may be related to the physical capabilities of the component. Some components may have limits on activation duration, for example. The analysis engine may also access additional sensor data 208. Sensor data may include sensors that provide the location of a user in a home or the temperature of the home. Sensor data 208 may include data outside of the home that may be received via internet such as wind conditions, humidity, weather conditions, and the like.

The analysis engine 210 may monitor gas sensor data 204. Gas sensor data 204 may be monitored to determine trends or baseline parameters. Gas sensor data may be monitored even if the detected gas levels are below safety thresholds. Small levels and fluctuations that may not directly cause human health concerns may be monitored. Readings may be monitored to determine trends with respect to time of the day, temperature, weather patterns, and the like. The readings may be compared or averaged over several days, weeks, or even months to establish baseline readings. Baseline readings may be continually refined.

The analysis engine may monitor gas sensor data 204 to identify high sensor readings and/or deviations from the baseline readings. Thresholds for high sensor readings may be configurable by a user and may be set to safety limit guidelines or a percentage of the safety limits such as 50% or 40%. When a threshold for a high sensor readings is exceeded by one or more of gas sensors the analysis engine 210 may trigger the user alert engine 214 to notify the user. The user alert engine 214 may generate indicators such as visual, audio, or tactile indicators to alert the user of the high readings. Alerts may be configured to be displayed on a display device connected to the central control. The alerts may be displayed on a television for example. Alerts may be pushed to a user's phone, smart watch, or other device. Alerts may include the location of the high readings, the duration of the high readings and the like. Alerts may be tailored based on the location of the user, the location of the alerting device, user profile, age of the user, and the like. For example, alerts pushed to a television receiver known to be in a child's room may be provided with a different alert than alerts on an adult's phone. Alerts for devices associated with children may have simple alerts that direct the user to exit the building while alerts associated with adults may include the location and severity of the readings.

In embodiments, alerts may be pushed or transmitted to other external parties. For example, landlord or a manager of building may receive alerts. The alerts may be configured to be transmitted to external parties after a period of time of the alerts being active. After 5 or 15 seconds of activity of the alert without any confirmation or disabling of the alarm the alarm may be transmitted to a wider set of recipients which may include a tenant who could be a business tenant, the fire department, and the like.

The analysis engine 210, upon detecting high gas sensor readings, may cause activation of mitigation actions. Mitigation actions may include activating ventilation system, opening windows, and/or deactivating components such as heaters or furnaces that may be a source of the gases. Mitigation actions may depend on the location of the occupants of the home. Sensor data 208 may be used to locate the occupants in the home and activate ventilation systems to direct the gases away from the location of the occupants. During the mitigation, sensors may be continually or periodically monitored to determine the effectiveness of the mitigation efforts. For example, activating a ventilation system may increase the concentration of gases in some locations.

The analysis engine may monitor gas sensor data 204 to identify deviations from baseline readings. Deviations from baseline readings may indicate a potential future problem. Deviations from baseline readings may trigger the analysis engine to initiate diagnostics to determine a cause of the deviation. Deviations such as a sudden rise of gas level readings compared to the baseline readings may trigger diagnostics.

Diagnostics initiated by the analysis engine 210 may include various stages, phases, or alternatives. In one embodiment, the analysis engine may initiate diagnostics that analyze correlations between component activity and elevated gas sensor readings. The analysis engine may compare and/or compute correlations between the toxic gas sensor data 204 and the component activity data 206. In some cases correlations or dependencies may involve multiple components or may be inconclusive. In embodiments, the analysis engine 210 may cause the activity scheduler 212 to change the timing, duration, frequency, relative timing, or the like of the activity of the components. The activity scheduler may modify the normal activity of components to test correlations or dependencies of multiple components.

Figure 3:
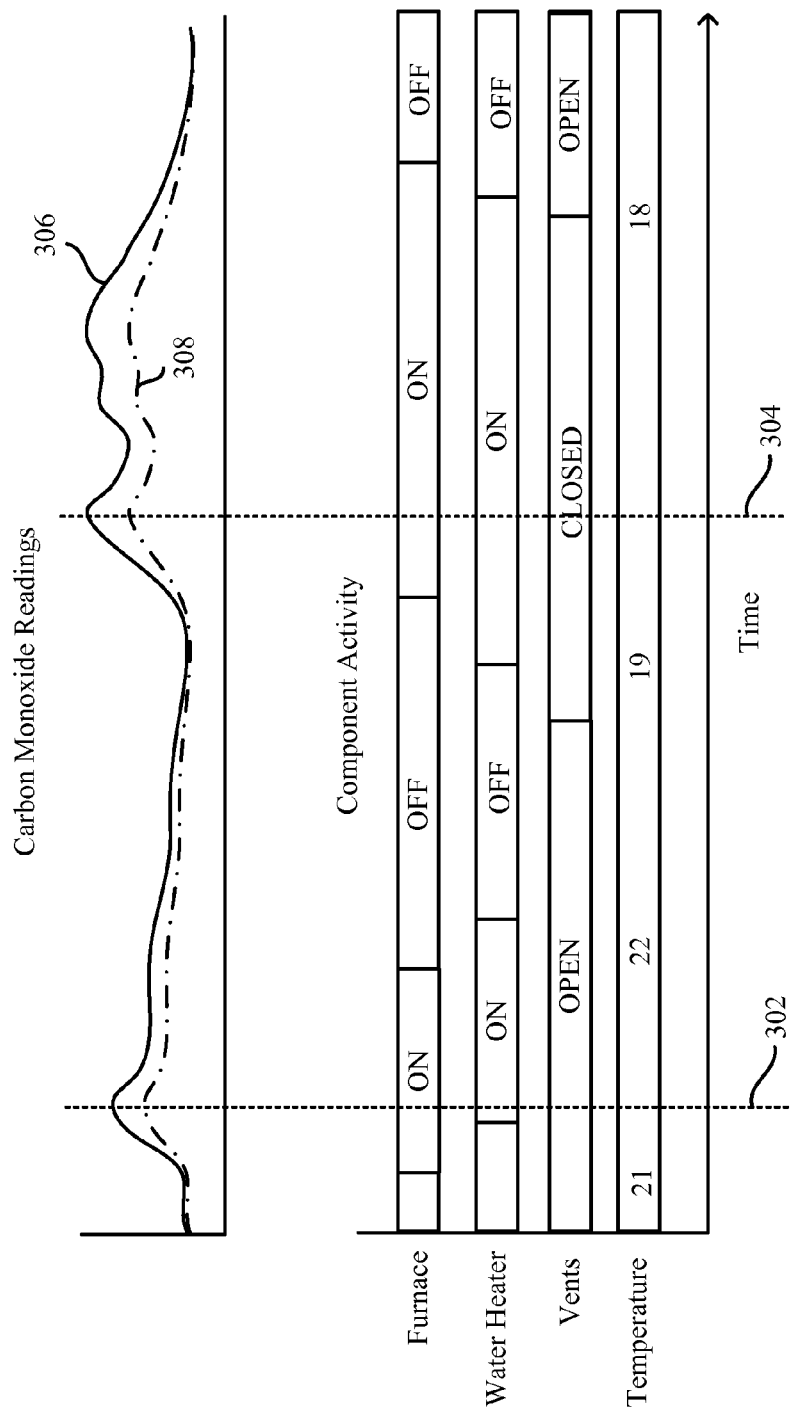
FIG. 3 illustrates an example scenario for diagnostics.

FIG. 3 depicts example scenario that may be used during diagnostics by the analysis engine 210. The analysis engine may receive and monitor gas sensor readings such as carbon monoxide sensor readings and component activity. The gas sensor readings may include current readings 306 and baseline readings 308. The analysis engine may analyze the sensor readings 306 to identify points that substantially differ from the baseline readings 308 and/or exceed a threshold value. Variations from baseline readings, such as an increase of more than 10% or more compared to the baseline readings may trigger the analysis engine to initiate diagnostics. In the example of FIG. 3, the current readings 306 differ from the baseline readings 308. The analysis engine may identify the main areas or periods of time 302, 303 in which the variations are observed. The analysis engine may compare the times of the increased sensor readings with the component activity to determine possible cause. In this example, the component activity includes the activity of four components; furnace, water heater, vents, and temperature readings. The component activity my show the times and durations when each component was active, sensor readings from each component, and the like. In some cases, the activity of some components may be inferred from the activity or readings of other components or sensors. The activity of the furnace, for example, may be inferred from the temperature readings, for example.

The analysis engine may compare the activity of the components and sensor readings to identify activity of components that correspond to or correlate to the periods of time 306, 308 of elevated readings. In the example of FIG. 3, the elevated sensor readings match the activity of two components; the furnace and the water heater. The periods of time 306, 308 of the elevated readings correlate to the times when the furnace and the water heater are on. Based on the correlation of two components to the elevated readings it may be unclear as to the real cause. The furnace may be causing the elevated readings, only the water heater, or there may be a dependence of the two components that cause a malfunction.

Based on the initial correlations, the analysis engine may initiate diagnostics procedures to verify the correlations and/or evaluate dependencies between component activity. Diagnostic procedures may include determining and initiating an alternative activity schedule of the components. The activity schedule may be configured with change the relative timing, the duration of the activity, and other parameter of component activity. For example, to determine which one, or if both of the furnace and water heater may have caused the elevated gas readings in FIG. 3, an alternative schedule may be used for further diagnostics. The alternative schedule may be arranged such that the activity of the furnace and the water heater do not coincide.

Figure 4:
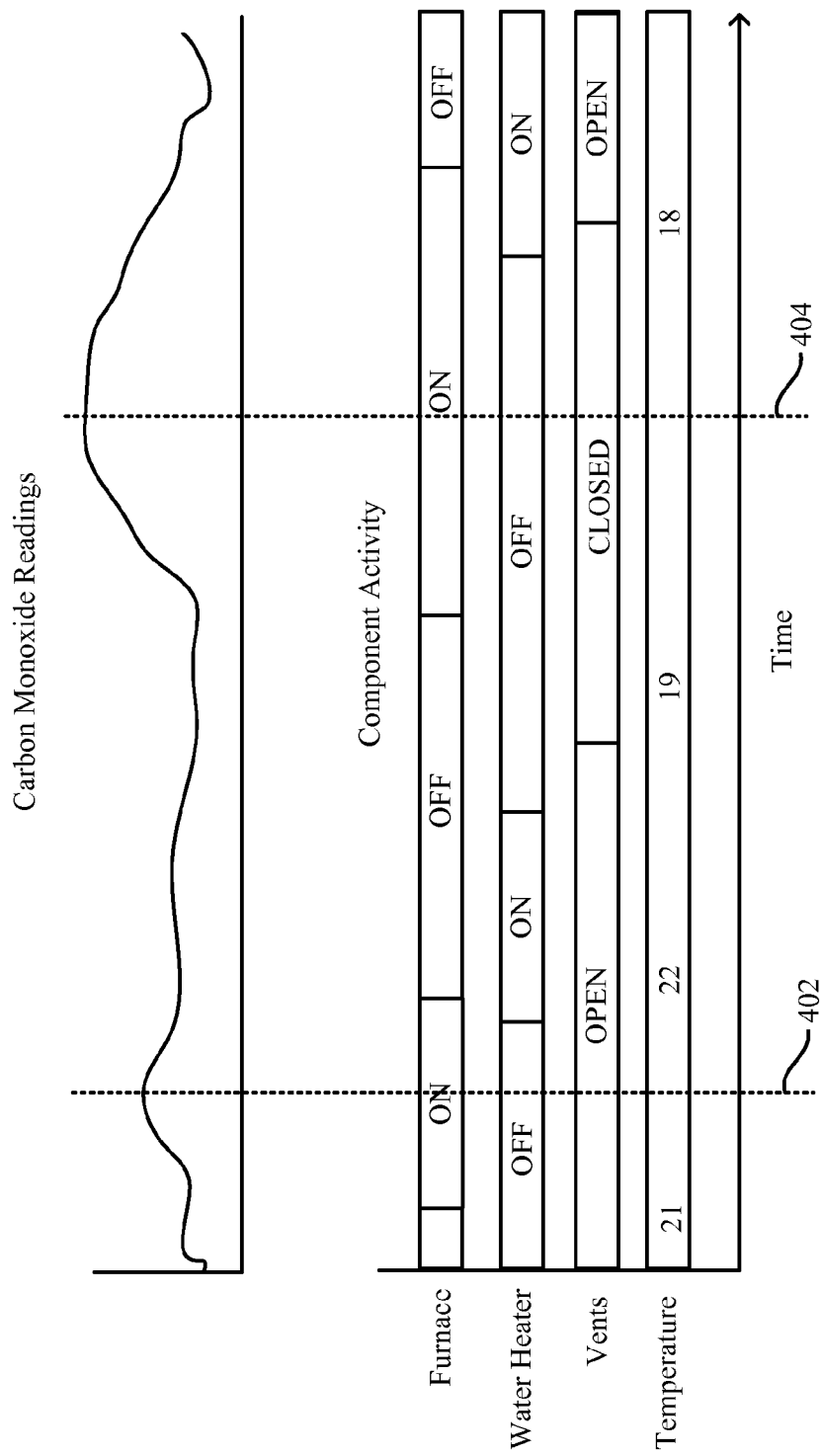
FIG. 4 illustrates an example scenario for diagnostics.

FIG. 4 depicts an example scenario with an alternative activity schedule for components. The alternative activity schedule may resting the furnace and the water heater to be ON during different time periods. During the activity of the alternative schedule, the analysis engine may monitor and analyze the gas sensor readings and compare them to the activity of the components. In the example of FIG. 4, the carbon monoxide readings still show two time periods 402, 404 of elevated levels. The two periods 402, 404 are correlated to the activity of the furnace and not the hot water heater. Additional alternative schedules may be used which change the timing of the activity of the furnace.

Figure 5:
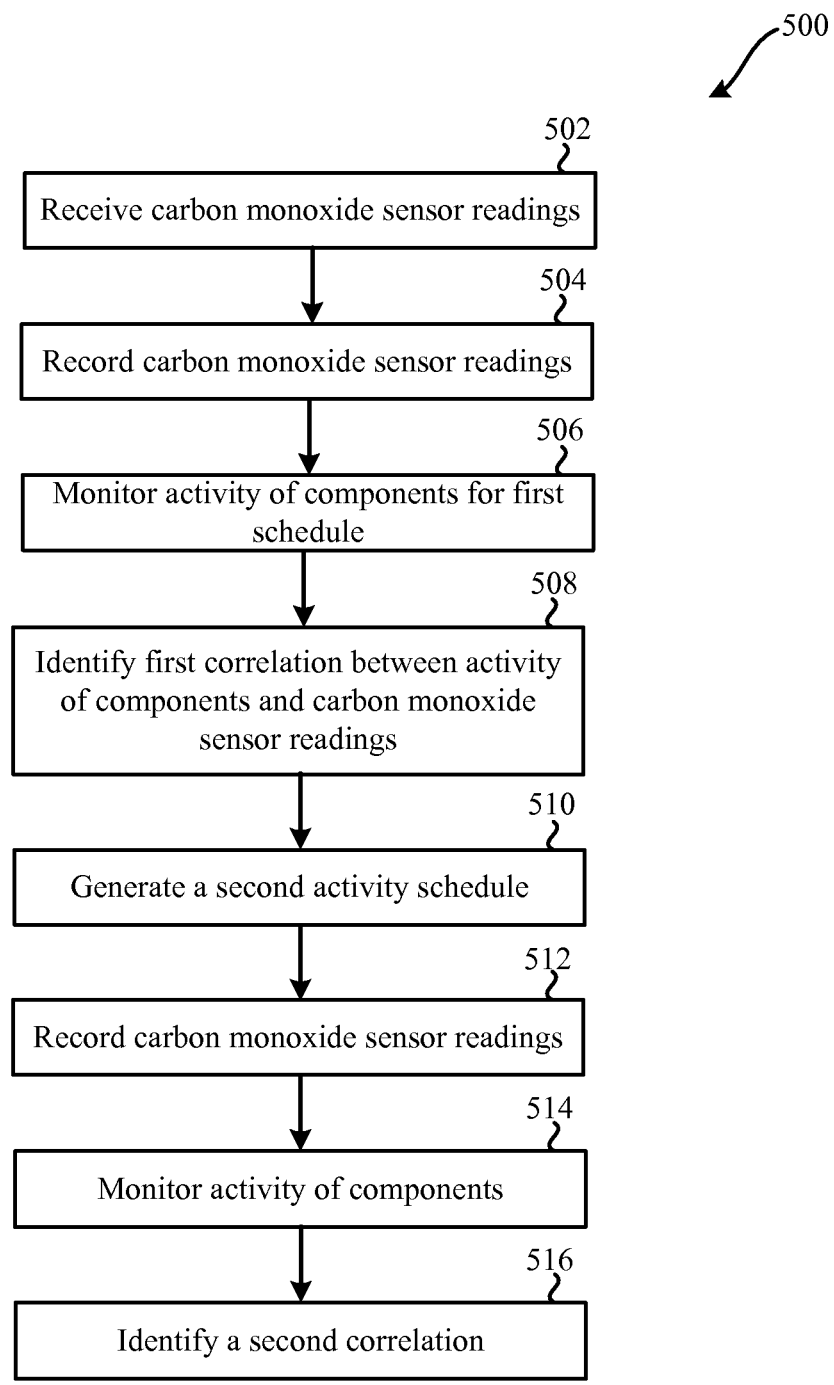
FIG. 5 illustrates an embodiment of a method for automation control for carbon monoxide diagnosis.

Various methods may be performed using system 100 of FIG. 1 and the module 200 of FIG. 2. FIG. 5 illustrates an embodiment of a method 500 for automation control for carbon monoxide diagnosis. Each step of method 500 may be performed by a computer system, such as computer system 800 of FIG. 8. Means for performing method 500 can include one or more computing devices functioning in concert, such as in a distributed computing arrangement.

At step 502 carbon monoxide sensor readings may be received and recorded in step 504. The readings may be continuously recorded or recorded only when changes in readings are observed. Each reading may be time stamped. At step 506, the activity of components may be monitored. In some cases the activity of the components may be determined from an activity schedule and the activity may not be directly recorded or monitored but inferred from the schedule. At step 508 the sensor readings and the activity of components may be analyzed to determine correlations, dependencies, causalities, and the like. Based at least in part on the determined correlations, a second activity schedule may be generated in step 510. The second activity schedule may include specific timing of the activity of components such as specific time of the day when a component should turn on or off. In some embodiments, the activity schedule may include constraints or even relative constrains on the activity of components. The relative constraints, for example, may indicate that whenever one component is on the other component must be off.

At step 512 the carbon monoxide sensor readings and the activity of components in step 514 may be monitored and recorded during the second activity schedule. At step 516 the sensor readings and the activity of components may be analyzed to identify correlations, dependencies, causalities, and the like. The correlations may be compared to the correlations identified in step 508 to determine if a change in the activity schedule changed the correlations.

Figure 6:
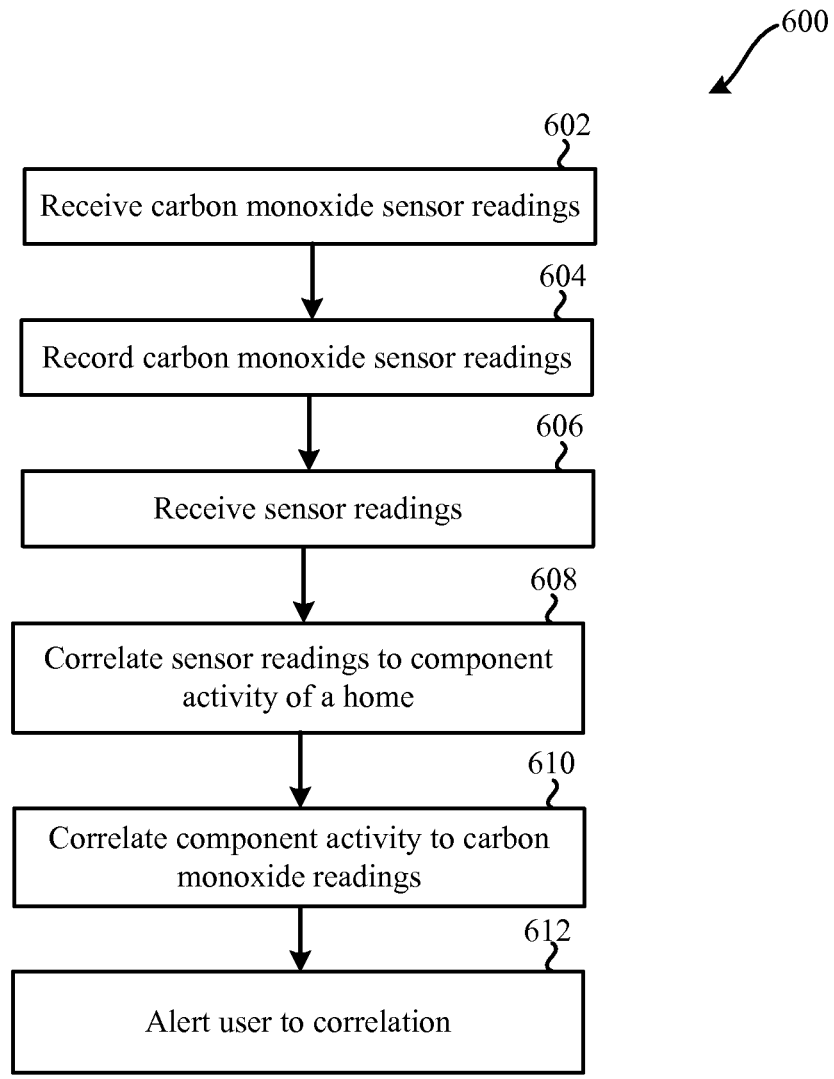
FIG. 6 illustrates an embodiment of a method for automation control for carbon monoxide diagnosis and alerting of a user.

FIG. 6 illustrates an embodiment of a method 600 for automation control for carbon monoxide diagnosis and alerting of a user. Each step of method 600 may be performed by a computer system, such as computer system 800 of FIG. 8. Means for performing method 600 can include one or more computing devices functioning in concert, such as in a distributed computing arrangement.

At step 602 carbon monoxide sensor readings may be received and recorded in step 604. In step 606 additional sensor readings may be received. Additional sensor readings may include sensors from the home such as temperature sensors, humidity sensors, and the like. Sensor readings may be indicative of the activity of components the system does not have direct control of. At step 608 the sensor readings may be used to determine the activity of components of the home that may not be directly monitored or controlled by a home automation system. At step 610 the determined activity of components may be correlated or compared to the carbon monoxide sensor readings. Activity of some components may correlate to elevated levels of carbon monoxide readings. The elevated levels may results from malfunction of a component. At step 612, the user may be alerted to any correlations between elevated carbon monoxide readings activity of the components.

Figure 7:
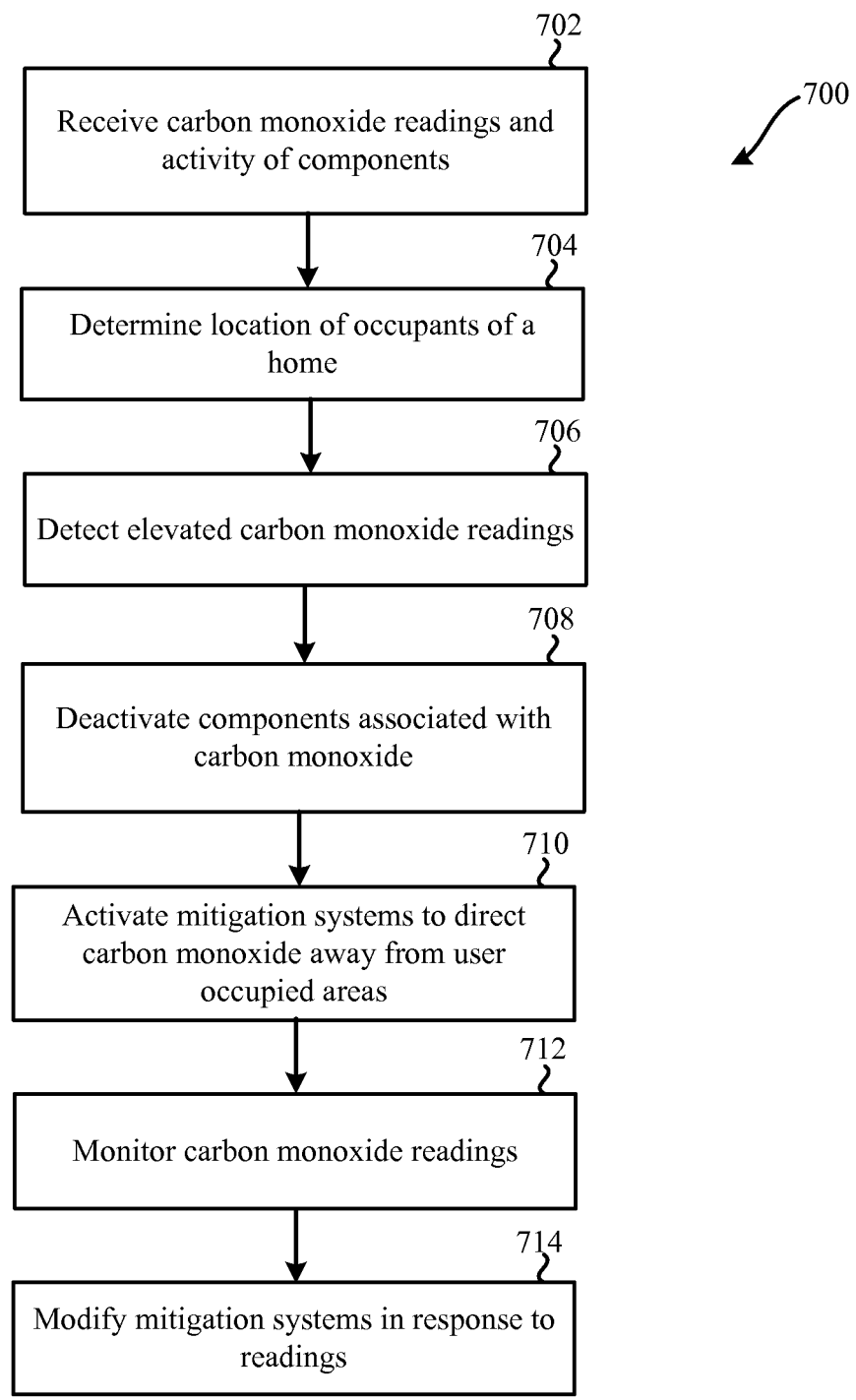
FIG. 7 illustrates an embodiment of a method for automation control for carbon monoxide mitigation.

FIG. 7 illustrates an embodiment of a method 700 for automation control for carbon monoxide mitigation. Each step of method 700 may be performed by a computer system, such as computer system 800 of FIG. 8. Means for performing method 700 can include one or more computing devices functioning in concert, such as in a distributed computing arrangement.

At step 702 carbon monoxide sensor readings may be received and recorded. At step 704 the location of occupants of a home may be determined using other systems of the house. If the user location cannot be directly determined the system may use historical data to identify a likely location of the user for the given time of the day, week, or the like. At step 706 the carbon monoxide readings may be monitored until elevated readings are identified. When the readings exceed thresholds that may be determined to be unsafe for occupants of a home components that may be a possible source of the carbon monoxide may be deactivated in step 708. At step 710 mitigation system or mitigation procedures may be activated. Mitigation system may include ventilation system, activation of window openings, and the like. The activation of the mitigation system may be activated to reduce the carbon monoxide from the area of the home where the user is determined to be present. Vents, windows, and the like may be activated to direct air flow in the home away from the user occupied areas. At step 712 the carbon monoxide sensor readings may be further monitored to determine if the mitigation systems and procedures have the intended effect and they me adjusted at step 714 accordingly.

It should be understood that although the methods and examples described herein used a home automation system other environments may also benefit from the methods and systems described. Toxic gas detection and mitigation may be useful for in industrial or commercial settings for example. Hotels, apartment buildings, and other structures may benefit for the techniques described herein. It should be understood that although the methods and examples described herein used carbon monoxide as a target for detection and mitigation any other toxic gas such as carbon dioxide, methane, and the like may also be the subject of the techniques and system described herein.

Figure 8:
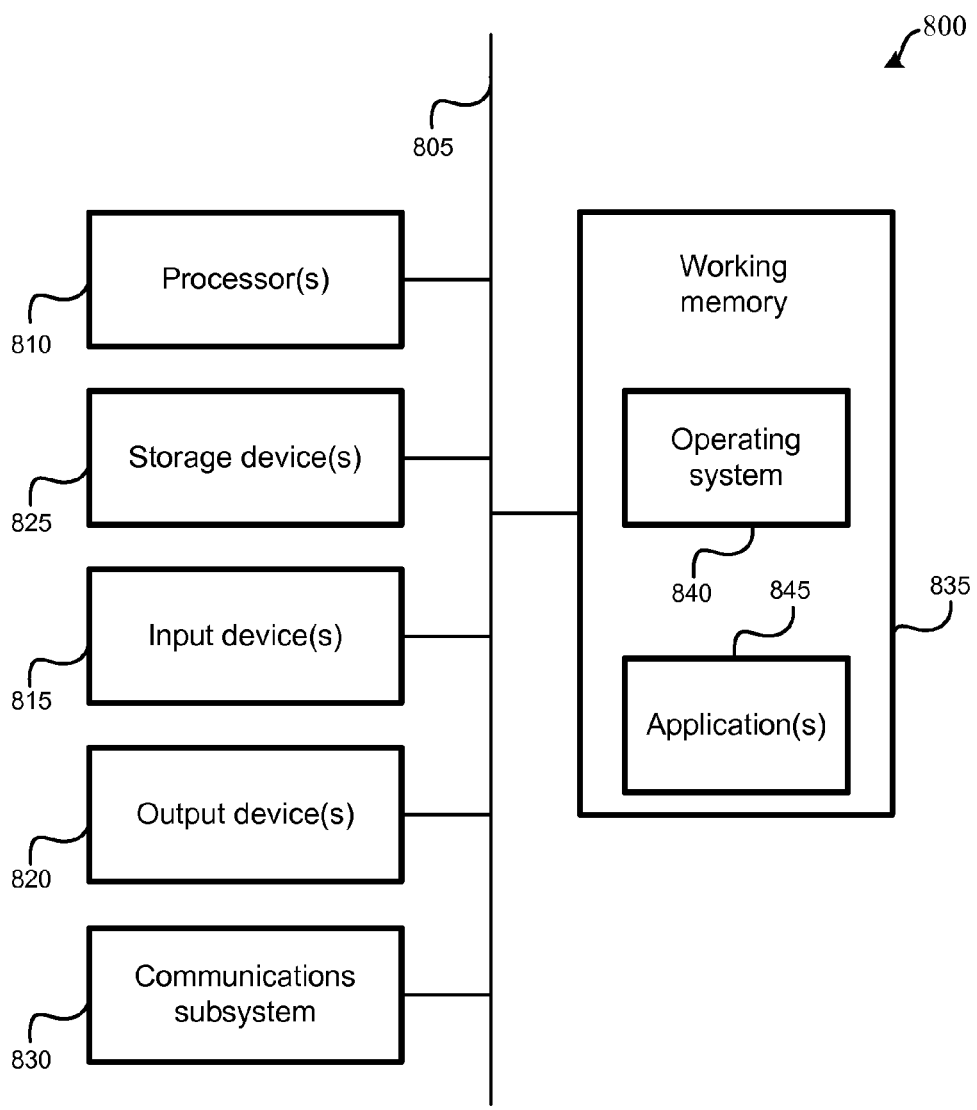
FIG. 8 illustrates an embodiment of a computer system.

A computer system as illustrated in FIG. 8 may be incorporated as part of the previously described computerized devices, such as the described television receivers. FIG. 8 provides a schematic illustration of one embodiment of a computer system 800 that can perform various steps of the methods provided by various embodiments. It should be noted that FIG. 8 is meant only to provide a generalized illustration of various components, any or all of which may be utilized as appropriate. FIG. 8, therefore, broadly illustrates how individual system elements may be implemented in a relatively separated or relatively more integrated manner.

The computer system 800 is shown comprising hardware elements that can be electrically coupled via a bus 805 (or may otherwise be in communication, as appropriate). The hardware elements may include one or more processors 810, including without limitation one or more general-purpose processors and/or one or more special-purpose processors (such as digital signal processing chips, graphics acceleration processors, video decoders, and/or the like); one or more input devices 815, which can include without limitation a mouse, a keyboard, remote control, and/or the like; and one or more output devices 820, which can include without limitation a display device, a printer, and/or the like.

The computer system 800 may further include (and/or be in communication with) one or more non-transitory storage devices 825, which can comprise, without limitation, local and/or network accessible storage, and/or can include, without limitation, a disk drive, a drive array, an optical storage device, a solid-state storage device, such as a random access memory ("RAM"), and/or a read-only memory ("ROM"), which can be programmable, flash-updateable and/or the like. Such storage devices may be configured to implement any appropriate data stores, including without limitation, various file systems, database structures, and/or the like.

The computer system 800 might also include a communications subsystem 830, which can include without limitation a modem, a network card (wireless or wired), an infrared communication device, a wireless communication device, and/or a chipset (such as a Bluetooth™ device, an 802.11 device, a WiFi device, a WiMax device, cellular communication device, etc.), and/or the like. The communications subsystem 830 may permit data to be exchanged with a network (such as the network described below, to name one example), other computer systems, and/or any other devices described herein. In many embodiments, the computer system 800 will further comprise a working memory 835, which can include a RAM or ROM device, as described above.

The computer system 800 also can comprise software elements, shown as being currently located within the working memory 835, including an operating system 840, device drivers, executable libraries, and/or other code, such as one or more application programs 845, which may comprise computer programs provided by various embodiments, and/ or may be designed to implement methods, and/or configure systems, provided by other embodiments, as described herein. Merely by way of example, one or more procedures described with respect to the method(s) discussed above might be implemented as code and/or instructions executable by a computer (and/or a processor within a computer); in an aspect, then, such code and/or instructions can be used to configure and/or adapt a general purpose computer (or other device) to perform one or more operations in accordance with the described methods.

A set of these instructions and/or code might be stored on a non-transitory computer-readable storage medium, such as the non-transitory storage device(s) 825 described above. In some cases, the storage medium might be incorporated within a computer system, such as computer system 800. In other embodiments, the storage medium might be separate from a computer system (e.g., a removable medium, such as a compact disc), and/or provided in an installation package, such that the storage medium can be used to program, configure, and/or adapt a general purpose computer with the instructions/code stored thereon. These instructions might take the form of executable code, which is executable by the computer system 800 and/or might take the form of source and/or installable code, which, upon compilation and/or installation on the computer system 800 (e.g., using any of a variety of generally available compilers, installation programs, compression/decompression utilities, etc.), then takes the form of executable code.

It will be apparent to those skilled in the art that substantial variations may be made in accordance with specific requirements. For example, customized hardware might also be used, and/or particular elements might be implemented in hardware, software (including portable software, such as applets, etc.), or both. Further, connection to other computing devices such as network input/output devices may be employed.

As mentioned above, in one aspect, some embodiments may employ a computer system (such as the computer system 800) to perform methods in accordance with various embodiments of the invention. According to a set of embodiments, some or all of the procedures of such methods are performed by the computer system 800 in response to processor 810 executing one or more sequences of one or more instructions (which might be incorporated into the operating system 840 and/or other code, such as an application program 845) contained in the working memory 835. Such instructions may be read into the working memory 835 from another computer-readable medium, such as one or more of the non-transitory storage device(s) 825. Merely by way of example, execution of the sequences of instructions contained in the working memory 835 might cause the processor(s) 810 to perform one or more procedures of the methods described herein.

The terms "machine-readable medium," "computer-readable storage medium" and "computer-readable medium," as used herein, refer to any medium that participates in providing data that causes a machine to operate in a specific fashion. These mediums may be non-transitory. In an embodiment implemented using the computer system 800, various computer-readable media might be involved in providing instructions/code to processor(s) 810 for execution and/or might be used to store and/or carry such instructions/code. In many implementations, a computer-readable medium is a physical and/or tangible storage medium. Such a medium may take the form of a non-volatile media or volatile media. Non-volatile media include, for example, optical and/or magnetic disks, such as the non-transitory storage device(s) 825. Volatile media include, without limitation, dynamic memory, such as the working memory 835.

Common forms of physical and/or tangible computer-readable media include, for example, a floppy disk, a flexible disk, hard disk, magnetic tape, or any other magnetic medium, a CD-ROM, any other optical medium, any other physical medium with patterns of marks, a RAM, a PROM, EPROM, a FLASH-EPROM, any other memory chip or cartridge, or any other medium from which a computer can read instructions and/or code.

Various forms of computer-readable media may be involved in carrying one or more sequences of one or more instructions to the processor(s) 810 for execution. Merely by way of example, the instructions may initially be carried on a magnetic disk and/or optical disc of a remote computer. A remote computer might load the instructions into its dynamic memory and send the instructions as signals over a transmission medium to be received and/or executed by the computer system 800.

The communications subsystem 830 (and/or components thereof) generally will receive signals, and the bus 805 then might carry the signals (and/or the data, instructions, etc. carried by the signals) to the working memory 835, from which the processor(s) 810 retrieves and executes the instructions. The instructions received by the working memory 835 may optionally be stored on a non-transitory storage device 825 either before or after execution by the processor(s) 810.

It should further be understood that the components of computer system 800 can be distributed across a network. For example, some processing may be performed in one location using a first processor while other processing may be performed by another processor remote from the first processor. Other components of computer system 800 may be similarly distributed. As such, computer system 800 may be interpreted as a distributed computing system that performs processing in multiple locations. In some instances, computer system 800 may be interpreted as a single computing device, such as a distinct laptop, desktop computer, or the like, depending on the context.

The methods, systems, and devices discussed above are examples. Various configurations may omit, substitute, or add various procedures or components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Also, configurations may be described as a process which is depicted as a flow diagram or block diagram. Although each may describe the operations as a sequential process, many of the operations can be performed in parallel or concurrently. In addition, the order of the operations may be rearranged. A process may have additional steps not included in the figure. Furthermore, examples of the methods may be implemented by hardware, software, firmware, middleware, microcode, hardware description languages, or any combination thereof. When implemented in software, firmware, middleware, or microcode, the program code or code segments to perform the necessary tasks may be stored in a non-transitory computer-readable medium such as a storage medium. Processors may perform the described tasks.

Having described several example configurations, various modifications, alternative constructions, and equivalents may be used without departing from the spirit of the disclosure. For example, the above elements may be components of a larger system, wherein other rules may take precedence over or otherwise modify the application of the invention. Also, a number of steps may be undertaken before, during, or after the above elements are considered.

What is claimed is:

1. A method for automation control for carbon monoxide diagnosis, the method comprising:
   receiving, at an automation controller, carbon monoxide sensor readings from one or more carbon monoxide detectors;
   recording, by the automation controller, the carbon monoxide sensor readings over a first time period;
   monitoring, by the automation controller, activity of components of a home over the first time period, wherein the activity of the components is at least in part based on a first activity schedule and constrained by a user input;
   identifying, by the automation controller, a first correlation between the activity of the components of the home and the carbon monoxide sensor readings over the first time period;
   generating, by the automation controller, a second activity schedule for a second time period for at least one component of the home, wherein the second activity schedule defines second activity comprising active and inactive periods of time for the at least one component of the home, and wherein the automation controller, during the second activity schedule, is configured to:
      meet user constraints; and
      test the first correlation between the activity and the carbon monoxide sensor readings by activating or deactivating the at least one component of the home to follow the second activity schedule during the second time period to analyze the carbon monoxide sensor readings over the second time period in response to the second activity;
   recording, by the automation controller, the carbon monoxide sensor readings over the second time period;
   monitoring, by the automation controller, the activity of the components of the home over the second time period;
   identifying, by the automation controller, a second correlation between the activity of the components and the carbon monoxide sensor readings over the second time period; and
   determining, by the automation controller, if the first correlation and the second correlation are consistent.

2. The method of claim 1, further comprising:
   receiving external data for the first time period; and
   identifying a third correlation between external data and the carbon monoxide sensor readings over the first time period;
   wherein the external data comprises data selected from:
      weather data;
      temperature data; and
      wind data.

3. The method of claim 1, further comprising:
   monitoring readings of home sensors in the home;
   determining activity of home appliances based on readings of the home sensors; and
   determining a third correlation between the home sensor readings and the carbon monoxide sensor readings.

4. The method of claim 1, further comprising:
   activating a ventilation system when the carbon monoxide sensor readings exceed a threshold.

5. The method of claim 1, further comprising:
   reporting, to the user, if the first correlation and the second correlation is consistent.

6. The method of claim 1, wherein:
   the second activity schedule is configured to change the activity of the components from the first activity schedule of the home that were correlated to the carbon monoxide sensor readings.

7. The method of claim 1, wherein:
   the second activity schedule is configured to change relative timing of the activity of the components from the first activity schedule.

8. A non-transitory processor-readable medium for automation control for carbon monoxide diagnosis, the medium comprising processor-readable instructions configured to cause one or more processors to:
   receive carbon monoxide sensor readings from one or more carbon monoxide detectors;
   record the carbon monoxide sensor readings over a first time period;
   monitor activity of components of a home over the first time period, wherein the activity of the components is at least in part based on a first activity schedule and constrained by a user input;
   identify a first correlation between the activity of the components of the home and the carbon monoxide sensor readings over the first time period;
   generate a second activity schedule for a second time period for at least one component of the home, wherein the second activity schedule defines second activity comprising active and inactive periods of time for the at least one component of the home, and wherein, during the second activity schedule, the processor readable instructions are configured to cause the one or more processors to:
      meet user constraints; and
      test the first correlation between the activity and the carbon monoxide sensor readings by activating or deactivating the at least one component of the home to follow the second activity schedule during the second time period to analyze the carbon monoxide sensor readings over the second time period in response to the second activity;
   record the carbon monoxide sensor readings over the second time period;
   monitor the activity of the components of the home over the second time period;

identify a second correlation between the activity of the components and the carbon monoxide sensor readings over the second time period; and
determine if the first correlation and the second correlation are consistent.

9. The non-transitory processor-readable medium of claim 8, wherein the processor-readable instructions cause one or more processors to:
receive external data for the first time period; and
identify a third correlation between external data and the carbon monoxide sensor readings over the first time period;
wherein the external data comprises data selected from:
weather data;
temperature data; and
wind data.

10. The non-transitory processor-readable medium of claim 8, wherein the processor-readable instructions cause one or more processors to:
monitor readings of home sensors in the home;
determine activity of home appliances based on readings of the home sensors; and
determine a third correlation between the home sensor readings and the carbon monoxide sensor readings.

11. The non-transitory processor-readable medium of claim 8, wherein the processor-readable instructions cause one or more processors to:
activate a ventilation system when the carbon monoxide sensor readings exceed a threshold.

12. The non-transitory processor-readable medium of claim 8, wherein the processor-readable instructions cause one or more processors to:
report, to the user, if the first correlation and the second correlation is consistent.

13. The non-transitory processor-readable medium of claim 8, wherein the second activity schedule is configured to change the activity of the components from the first activity schedule of the home that were correlated to the carbon monoxide sensor readings.

14. The non-transitory processor-readable medium of claim 8, wherein the second activity schedule is configured to change relative timing of the activity of the components from the first activity schedule.

15. A television receiver configured for automation control for carbon monoxide diagnosis, the television receiver comprising:
one or more processors;
a memory communicatively coupled with and readable by the one or more processors and having stored therein processor-readable instructions which, when executed by the one or more processors, cause the one or more processors to:
receive carbon monoxide sensor readings from one or more carbon monoxide detectors;
record the carbon monoxide sensor readings over a first time period;
monitor activity of components of a home over the first time period, wherein the activity of the components is at least in part based on a first activity schedule and constrained by a user input;
identify a first correlation between the activity of the components of the home and the carbon monoxide sensor readings over the first time period;
generate a second activity schedule for a second time period for at least one component of the home, wherein the second activity schedule defines second activity comprising active and inactive periods of time for the at least one component of the home, and wherein during the second activity schedule, the processor-readable instructions cause the one or more processors to:
meet user constraints; and
test the first correlation between the activity and the carbon monoxide sensor readings by activating or deactivating the at least one component of the home to follow the second activity schedule during the second time period to analyze the carbon monoxide sensor readings over the second time period in response to the second activity;
record the carbon monoxide sensor readings over the second time period;
monitor the activity of the components of the home over the second time period;
identify a second correlation between the activity of the components and the carbon monoxide sensor readings over the second time period; and
determine if the first correlation and the second correlation are consistent.

16. The television receiver configured for automation control for carbon monoxide diagnosis of claim 15, wherein the processor-readable instructions, when executed, further cause the one or more processors to:
receive external data for the first time period; and
identify a third correlation between external data and the carbon monoxide sensor readings over the first time period;
wherein the external data comprises data selected from:
weather data;
temperature data; and
wind data.

17. The television receiver configured for automation control for carbon monoxide diagnosis of claim 15, wherein the processor-readable instructions, when executed, further cause the one or more processors to:
monitor readings of home sensors in the home;
determine activity of home appliances based on readings of the home sensors; and
determine a third correlation between the home sensor readings and the carbon monoxide sensor readings.

18. The television receiver configured for automation control for carbon monoxide diagnosis of claim 15, wherein the processor-readable instructions, when executed, further cause the one or more processors to activate a ventilation system when the carbon monoxide sensor readings exceed a threshold.

19. The television receiver configured for automation control for carbon monoxide diagnosis of claim 15, wherein the processor-readable instructions, when executed, further cause the one or more processors to report, to the user, if the first correlation and the second correlation is consistent.

20. The television receiver configured for automation control for carbon monoxide diagnosis of claim 15, wherein the second activity schedule is configured to change the activity of the components from the first activity schedule of the home that were correlated to the carbon monoxide sensor readings.

* * * * *